(12) United States Patent
Martin et al.

(10) Patent No.: US 10,850,054 B2
(45) Date of Patent: Dec. 1, 2020

(54) METHOD AND APPARATUS FOR TREATING HYPERAROUSAL DISORDERS

(71) Applicant: ResMed Pty Ltd, Bella Vista (AU)

(72) Inventors: Dion Charles Chewe Martin, Sydney (AU); Jeffrey Peter Armitstead, Sydney (AU); Dinesh Ramanan, Sydney (AU)

(73) Assignee: ResMed Pty Ltd

( * ) Notice: Subject to any disclaimer, the term of this patent is extended or adjusted under 35 U.S.C. 154(b) by 758 days.

(21) Appl. No.: 15/519,667

(22) PCT Filed: Oct. 26, 2015

(86) PCT No.: PCT/AU2015/050663
§ 371 (c)(1),
(2) Date: Apr. 17, 2017

(87) PCT Pub. No.: WO2016/065411
PCT Pub. Date: May 6, 2016

(65) Prior Publication Data
US 2017/0239433 A1    Aug. 24, 2017

(30) Foreign Application Priority Data

Oct. 27, 2014 (AU) .............................. 2014904281

(51) Int. Cl.
*A61M 16/00* (2006.01)
*A61M 16/16* (2006.01)
(Continued)

(52) U.S. Cl.
CPC .... *A61M 16/0069* (2014.02); *A61M 16/0051* (2013.01); *A61M 16/026* (2017.08);
(Continued)

(58) Field of Classification Search
CPC .............. A61M 16/022; A61M 16/024; A61M 16/026; A61M 16/0069; A61M 16/0021;
(Continued)

(56) References Cited

U.S. PATENT DOCUMENTS

| 4,944,310 A | 7/1990 | Sullivan |
| 6,532,959 B1 | 3/2003 | Berthon-Jones |

(Continued)

FOREIGN PATENT DOCUMENTS

| CN | 101104092 A | 1/2008 |
| CN | 101804232 A | 8/2010 |

(Continued)

OTHER PUBLICATIONS

Krakow B, Ulibarri VA, Romero EA. Patients With Treatment-Resistant Insomnia Taking Nightly Prescription Medications for Sleep: A Retrospective Assessment of Diagnostic and Treatment Variables. Prim. Care Companion J Clin Psychiatry, Jul. 2010: 12(4).

(Continued)

*Primary Examiner* — Timothy A Stanis
*Assistant Examiner* — Cana A Gallegos
(74) *Attorney, Agent, or Firm* — Botos Churchill IP Law, LLP

(57) ABSTRACT

Methods and apparatus provide automated controls for a respiratory pressure therapy device, such as a servo-ventilator. For example, a controller of a respiratory pressure therapy device may control application of pressure support ventilation therapy to an airway of a patient. The controller may control the respiratory pressure therapy device to auto-titrate an expiratory positive airway pressure (EPAP) of a pressure support ventilation therapy so as to maintain airway patency of the patient. The EPAP may be bounded below by a floor pressure limit. The controller may control (Continued)

the respiratory pressure therapy device to repeatedly adjust the floor pressure limit depending on events of interest during the auto-titration of the EPAP. Such methodologies may improve treatment for patients such as those suffering from sleep disordered breathing-comorbid hyperarousal disorders.

29 Claims, 23 Drawing Sheets

(51) Int. Cl.
*A61M 16/06* (2006.01)
*A61M 16/10* (2006.01)
*A61M 21/02* (2006.01)
*A61M 16/12* (2006.01)
*A61M 21/00* (2006.01)

(52) U.S. Cl.
CPC .......... *A61M 16/06* (2013.01); *A61M 16/105* (2013.01); *A61M 16/16* (2013.01); *A61M 21/02* (2013.01); *A61M 16/107* (2014.02); *A61M 16/125* (2014.02); *A61M 2016/003* (2013.01); *A61M 2016/0027* (2013.01); *A61M 2016/0036* (2013.01); *A61M 2021/0088* (2013.01); *A61M 2202/0208* (2013.01); *A61M 2205/15* (2013.01); *A61M 2205/18* (2013.01); *A61M 2205/3331* (2013.01); *A61M 2205/3365* (2013.01); *A61M 2205/3375* (2013.01); *A61M 2205/3561* (2013.01); *A61M 2205/3584* (2013.01); *A61M 2205/42* (2013.01); *A61M 2205/502* (2013.01); *A61M 2205/581* (2013.01); *A61M 2205/583* (2013.01); *A61M 2230/005* (2013.01); *A61M 2230/205* (2013.01); *A61M 2230/63* (2013.01)

(58) Field of Classification Search
CPC .. A61M 2016/0015; A61M 2016/0018; A61M 2016/0021; A61M 2016/0024; A61M 16/0066; A61M 2205/3341
USPC .................................................... 128/204.18
See application file for complete search history.

(56) References Cited

U.S. PATENT DOCUMENTS

| | | | |
|---|---|---|---|
| 7,089,937 B2 | 8/2006 | Berthon-Jones et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 2006/0000475 A1 | 1/2006 | Matthews et al. | |
| 2006/0011200 A1* | 1/2006 | Remmers ............ | A61M 16/026 128/204.23 |
| 2007/0215146 A1* | 9/2007 | Douglas ................ | A61M 16/06 128/200.24 |
| 2008/0308105 A1* | 12/2008 | Alder ..................... | A61B 5/097 128/204.23 |
| 2009/0038616 A1 | 2/2009 | Mulcahy et al. | |
| 2009/0095299 A1* | 4/2009 | Saldivar ............ | A61M 16/0051 128/204.23 |
| 2010/0108066 A1* | 5/2010 | Martin ................. | A61M 16/026 128/204.23 |
| 2011/0166470 A1 | 7/2011 | Rapoport et al. | |
| 2012/0097155 A1 | 4/2012 | Iyer | |
| 2012/0291785 A1* | 11/2012 | Ramanan .......... | A61M 16/0069 128/204.23 |
| 2013/0312754 A1* | 11/2013 | Garde ............... | A61M 16/0057 128/204.23 |
| 2014/0316191 A1 | 10/2014 | de Zambotti et al. | |

FOREIGN PATENT DOCUMENTS

| | | |
|---|---|---|
| CN | 101884046 A | 11/2010 |
| CN | 102665546 A | 9/2012 |
| CN | 102711887 A | 10/2012 |
| CN | 102711888 A | 10/2012 |
| CN | 103083770 A | 5/2013 |
| EP | 0705615 A1 | 4/1996 |
| EP | 1434548 A2 | 7/2004 |
| JP | 3566285 B2 | 6/2004 |
| WO | 9812965 A1 | 4/1998 |
| WO | 03030804 A2 | 4/2003 |
| WO | 2005063323 A1 | 7/2005 |
| WO | 2010097718 A1 | 9/2010 |
| WO | 2011006199 A1 | 1/2011 |
| WO | 2011086434 A1 | 7/2011 |
| WO | 2013020167 A1 | 2/2013 |
| WO | 2013152403 A1 | 10/2013 |
| WO | 2014095962 A1 | 6/2014 |
| WO | 2015150997 A1 | 10/2015 |
| WO | 2016029265 A1 | 3/2016 |

OTHER PUBLICATIONS

West, John B., "Respiratory Physiology: The Essentials", Jan. 2012, 9th Edition, Lippincott Williams & Wilkins, Baltimore, MD.
What is RESPeRATE? [retrieved from internet on Feb. 3, 2016] <URL: http://web.archive.org/web/20131010063624/http://www.resperate.com/what-is-resperate/> published on Oct. 10, 2013, as per Wayback Machine.
International Search Report for Application No. PCT/AU2015/050663 dated Feb. 10, 2016.
Extended European Search Report for EP Application No. 15855453, dated Jun. 26, 2018.
Chinese Office Action issued in corresponding CN application No. 201580069232.5 dated Jan. 7, 2019.
Chinese Office Action issued in corresponding CN application No. 201580069232.5 dated Jul. 10, 2019.

* cited by examiner

METHOD AND APPARATUS FOR TREATING HYPERAROUSAL DISORDERS

1. CROSS-REFERENCE TO RELATED APPLICATIONS

The present application is a national phase entry under 35 U.S.C. § 371 of International Application No. PCT/AU2015/050663 filed Oct. 26, 2015, published in English, which claims the benefit of and priority to Australian Patent Application No. 2014904281 filed Oct. 27, 2014, all of which are incorporated herein by reference.

2. STATEMENT REGARDING FEDERALLY SPONSORED RESEARCH OR DEVELOPMENT

Not Applicable

3. THE NAMES OF PARTIES TO A JOINT RESEARCH DEVELOPMENT

Not Applicable

4. SEQUENCE LISTING

Not Applicable

5. BACKGROUND OF THE TECHNOLOGY 5.1 Field of the Technology

The present technology relates to one or more of the detection, diagnosis, treatment, prevention and amelioration of respiratory-related disorders. In particular, the present technology relates to medical devices or apparatus, and their use.

5.2 Description of the Related Art
Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones). CSR is a form of periodic breathing.

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

A range of therapies have been used to treat or ameliorate such conditions. Furthermore, otherwise healthy individuals may take advantage of such therapies to prevent respiratory disorders from arising.

5.2.1.1 Insomnia

Insomnia is defined as problems falling asleep and staying asleep, or as non-restorative sleep, that persist(s) longer than one month and result(s) in functional impairment. Two kinds of insomnia are defined: (i) sleep onset insomnia, i.e. difficulty falling asleep; (ii) sleep maintenance insomnia, i.e. frequent awakenings during the night or early morning awakenings. Insomnia can be acute, intermittent, or chronic (duration greater than six months). Chronic insomnia is a common complaint in the general population (prevalence may be between 6% and 18%) as well as in various subpopulations such as the elderly, psychiatric patients, and shift workers. A current theory of insomnia is that due to any number of reasons, insomniacs are in a state of physiologic hyperarousal over the 24-hour period, and that this hyperarousal leads to sleep disturbances. Insomnia can occur as a symptom of another disorder, as a disorder in its own right, or both. Insomnia that begins as a symptom of another disorder (comorbid insomnia) can develop into a disorder in its own right.

Insomnia is frequently associated with psychological disorders. In Krakow's 2010 study, 87% of insomnia patients reported a history of at least one of the following: depression, anxiety disorder, post-traumatic stress disorder (PTSD), panic disorder, schizophrenia, bipolar disorder, obsessive-compulsive disorder (OCD), traumatic exposure, or claustrophobia.

Many—but not all—studies have shown higher than expected rates of comorbid SDB with hyperarousal disorders, in particular chronic insomnia, even though the subjects may not report excessive sleepiness.

5.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of uncomfortable, difficult to use, expensive or aesthetically unappealing.

Non-invasive ventilation (NIV) provides ventilatory support to a patient through the upper airways to assist patient's breathing and/or maintain adequate oxygen levels in the body by doing some or all of the work of breathing. The ventilatory support is provided via a non-invasive patient interface. NIV has been used to treat OSA, respiratory failure, and periodic breathing. In some forms, the comfort and effectiveness of these therapies may be improved.

Evidence for cognitive-behavioural therapy (CBT) as the ideal first-line treatment for insomnia is substantial, but the lack of behavioural sleep medicine specialists both at sleep medical centres and in the medical community at large has limited its application. In contrast, pharmacotherapy for insomnia is well established. Traditional standards indicate prescribed medication for acute, transient, or situational insomnia, and the prescribing instructions may recommend nightly use for a few weeks or a few times per week for longer intervals.

However, a sizable proportion of insomniacs may not experience adequate symptomatic relief despite continuing to use nightly prescription medications.

If it is suspected that insomnia is comorbid with SDB, respiratory pressure therapy may be attempted. Whether SDB is cause or effect of insomnia can be debated, but it has been shown that fully resolving the comorbid SDB can ameliorate insomnia. By treating the SDB, thereby assisting the patient to achieve consolidated REM sleep, respiratory pressure therapy can also alleviate any psychological comorbidities.

In particular, CPAP therapy, and more recently, adaptive servo-ventilation (ASV) therapy have been proposed for insomnia comorbid with SDB, both acute and chronic. However, among insomniacs, tolerance of, and adherence to, traditional respiratory pressure therapy is typically low. The obvious challenge facing respiratory pressure therapy in the context of insomnia is that a respiratory pressure therapy itself may be a potential source of sleep disturbance, both for sleep onset and throughout the night, at least during the initial phase of acclimatization.

5.2.3 Treatment Systems

The pathway to receiving respiratory pressure therapy may involve a diagnosis system to positively diagnose the relevant condition, a titration system to titrate efficacious therapy settings, and a treatment system for the individual to use at home.

A treatment system may comprise a Respiratory Pressure Therapy Device (RPT device), an air circuit, a humidifier, a patient interface, and data management.

5.2.3.1 Patient Interface

A patient interface may be used to interface respiratory equipment to its user, for example by providing a flow of air to an entrance to the airways. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH$_2$O. For other forms of therapy, such as the delivery of oxygen, the patient interface may not include a seal sufficient to facilitate delivery to the airways of a supply of gas at a positive pressure of about 10 cmH$_2$O.

5.2.3.2 Respiratory Pressure Therapy (RPT) Device

One known RPT device used for treating sleep disordered breathing is the S9 Sleep Therapy System, manufactured by ResMed. Another example of an RPT device is a non-invasive ventilator.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

5.2.3.3 Humidifier

Delivery of a flow of air without humidification may cause drying of airways. The use of a humidifier with a RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

5.2.4 Diagnosis and Monitoring Systems

Diagnosis is the identification of a condition from its signs and symptoms. Diagnosis tends to be a one-off process, whereas monitoring the progress of a condition can continue indefinitely. Some diagnosis systems are suitable only for diagnosis, whereas some may also be used for monitoring.

Polysomnography (PSG) is a conventional system for diagnosis and prognosis of sleep disorders, and typically involves expert clinical staff to both apply and/or interpret. PSG typically involves the placement of 15 to 20 contact sensors on a person in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. However, while they may be suitable for their usual application in a clinical setting, PSG systems are complicated and potentially expensive, and/or may be uncomfortable or impractical for patients trying to sleep at home, particularly insomnia patients.

The disparity in the reported incidence of SDB in chronic insomnia patients may be related to the method of diagnosis, since comorbid SDB in such insomniacs can be challenging to successfully diagnose: conventional scoring based on the apnea-hypopnea index (AHI) may not be sensitive to SDB in this group, even under conventional polysomnography.

6. BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

The present technology generally relates to apparatus and methods used in the diagnosis, amelioration, treatment or prevention of hyperarousal disorders.

In what follows, the term "insomnia" is used to stand in for all hyperarousal disorders including insomnia, anxiety, and PTSD, except where indicated otherwise.

One aspect of the present technology comprises methods and apparatus for acclimatizing an SDB-comorbid insomnia patient to respiratory pressure therapy by means of paced breathing. The paced breathing may be combined with biofeedback. Such acclimatization methods and apparatus may also be useful as a calming intervention, either during daytime sessions, before going to sleep, or upon awakening during the night.

Another aspect of the present technology comprises methods and apparatus for effective therapy for SDB-comorbid insomnia, comprising pressure support ventilation with an adaptive ventilation target and auto-titration of expiratory pressure. The expiratory pressure of the pressure support ventilation is auto-titrated above a floor pressure limit that is variable. The floor pressure limit may be repeatedly adjusted depending on events of interest during auto-titration. Alternatively, the floor pressure limit may be repeatedly adjusted depending on the increments to the expiratory pressure during a preceding analysis interval. The pressure support ventilation therapy may be substituted with acclimatization therapy, e.g. paced breathing with biofeedback, while the patient is awake.

Another aspect of the present technology comprises methods and apparatus for effective therapy for SDB-comorbid insomnia, comprising servo-ventilation in which the gain of the servo-ventilation control is variable depending on the sleep state of the patient.

Some versions of the present technology concern a method of determining a floor pressure limit for EPAP pressure of a respiratory pressure therapy device, such as for patients with SDB-comorbid hyperarousal disorders. The method may include monitoring pressure support ventilation therapy of a respiratory pressure therapy device that auto-titrates an EPAP of the pressure support ventilation therapy to maintain airway patency of the patient. The method may include repeatedly, in a controller, determining an adjusted floor pressure limit depending on events of interest occurring during monitoring of auto-titration of the EPAP. Optionally, the method may further include delivering the EPAP so as to be greater than or equal to the adjusted floor pressure limit.

Some versions of the present technology may include a method of control of a respiratory pressure therapy device to treat SDB-comorbid hyperarousal disorders in a patient. The method may include controlling application of pressure support ventilation therapy to an airway of the patient by a respiratory pressure therapy device. The method may include controlling the respiratory pressure therapy device to auto-titrate an EPAP of the pressure support ventilation therapy so as to maintain airway patency of the patient, such that the EPAP is bounded below by a floor pressure limit. The method may include controlling the respiratory pressure therapy device to repeatedly adjust the floor pressure limit depending on events of interest during the auto-titration of the EPAP.

In some versions, the events of interest may be increments to the EPAP, and the repeated adjustment of the floor pressure limit involve repeatedly: forming a distribution of EPAP values at which increments to the EPAP occurred over an analysis interval, and adjusting the floor pressure limit based on statistical analysis of the distribution. The adjustment of the floor pressure limit may be based on a mode of the distribution. The analysis interval may be a night of pressure-support ventilation therapy with auto-titrating EPAP. The adjustment to the floor pressure limit may be dependent on a current value of the EPAP. An adjustment to the floor pressure limit may be dependent on a number of events of interest that occur in a predetermined interval during the auto-titration of the EPAP. The adjustment to the floor pressure limit may include incrementing the floor pressure limit if a predetermined number of events of interest occur within the predetermined interval. The incrementing of the floor pressure limit may include increasing the floor pressure to a current value of the EPAP.

In some versions, the events of interest may be SDB events. The events of interest may be increments to the EPAP as a result of the auto-titration of the EPAP. The method may also include determining, in the respiratory pressure therapy device, a sleep state of the patient. The auto-titrating of the EPAP may involve not decreasing the EPAP while the patient is determined to be in an asleep state.

Optionally, the pressure support ventilation therapy may be applied dependent on the sleep state of the patient. The respiratory pressure therapy device may apply pressure support ventilation therapy when the patient is determined to be in an asleep state, and the respiratory pressure therapy device may apply an acclimatization therapy when the patient is determined to be in an awake state. The acclimatization therapy may be paced breathing. The paced breathing may be combined with biofeedback matched to an interim breathing rate target of the paced breathing. The biofeedback may be in one or more of acoustic and visual form.

In some cases, the method may include applying the pressure support ventilation therapy on receiving, by the respiratory pressure therapy device, a command from the patient. The command may be activation of a manual control. The command may be a sound emitted by the patient. The command may be a voluntary respiratory manoeuvre by the patient.

Some versions of the present technology may include a method of control of a servo-ventilator to treat SDB-comorbid hyperarousal disorders in a patient. The method may include controlling a servo-ventilator to servo-ventilate the patient using a servo-ventilation control gain. The method may include determining a sleep state of the patient. The servo-ventilation control gain may be variable depending on the determined sleep state. In some cases, the servo-ventilation control gain may be relatively low when the patient is determined to be in an awake state, and may be relatively high when the patient is determined to be in an asleep state.

Some versions of the present technology may include a method of acclimatizing a patient to pressure support ventilation therapy. The method may include applying paced breathing to an airway of the patient by a respiratory pressure therapy device. The method may include providing biofeedback to the patient, wherein the biofeedback is matched to an interim breathing rate target of the paced breathing.

In some versions, the biofeedback may be in one or more of acoustic and visual form. The method may include terminating the paced breathing on receiving a command from the patient. The command may be activation of a manual control. The command may be a sound emitted by the patient. The command may be a voluntary respiratory manoeuvre by the patient.

Some versions of the present technology may include an SDB-comorbid hyperarousal treatment apparatus. The apparatus may include a pressure generator configured to deliver a flow of air at a controllable treatment pressure above atmospheric to an airway of a patient via a patient interface over an air circuit. The apparatus may include a controller. The controller may be configured to control the treatment pressure of the flow of air so as to apply pressure support ventilation therapy to the airway of the patient. The controller may be configured to auto-titrate an EPAP of the pressure support ventilation therapy so as to maintain airway patency of the patient, such that the EPAP is bounded below by a floor pressure limit. The controller may be configured to repeatedly adjust the floor pressure limit depending on events of interest during the auto-titration of the EPAP.

Some versions of the apparatus may include a sensor configured to generate a signal representative of a physiological characteristic of the patient. The controller may be further configured to determine a sleep state of the patient from the signal. The apparatus may include a user input device comprising a manual control. The apparatus may include an audio sensor. The apparatus may include a data communication interface through which the controller may be configured to communicate with a local external device. The controller may be configured to control the local external device to provide biofeedback to the patient. The controller may be configured to receive an audio signal from the local external device. The controller may be configured to receive a signal representative of a physiological characteristic of the patient from the local external device. The controller may be further configured to determine a sleep state of the patient from the signal.

Some versions of the present technology may include an SDB-comorbid hyperarousal treatment apparatus. The apparatus may include a pressure generator configured to deliver a flow of air at a controllable treatment pressure above atmospheric to an airway of a patient via a patient interface over an air circuit. The apparatus may include a controller configured to control the treatment pressure of the flow of air so as to servo-ventilate the patient using a servo-ventilation control gain. The controller may be configured to determine a sleep state of the patient. The servo-ventilation control gain may be variable depending on the determined sleep state.

Some versions of the present technology may include an apparatus. The apparatus may include a pressure generator configured to deliver a flow of air at a controllable treatment pressure above atmospheric to an airway of a patient via a patient interface over an air circuit. The apparatus may include a controller configured to control the treatment pressure of the flow of air so as to apply paced breathing to the airway of the patient. The controller may be configured to control the providing of biofeedback to the patient. The biofeedback may be matched to an interim breathing rate target of the paced breathing. The apparatus may include a user input device comprising a manual control. The controller may be further configured to terminate the paced breathing and the biofeedback on activation of the manual control. The apparatus may include an audio sensor. The controller may be further configured to terminate the paced breathing and the biofeedback upon the audio sensor detecting a predetermined sound. The apparatus may include a data communication interface through which the controller may be configured to communicate with a local external device. The controller may be configured to control the local external device to provide the biofeedback to the patient. The controller may be further configured to receive an audio signal from the local external device. The controller may be further configured to terminate the paced breathing and the biofeedback upon detecting a predetermined sound in the audio signal.

The methods/systems/devices/apparatus described herein can provide improved functioning in a processor, such as of a specific purpose computer, respiratory monitor and/or a respiratory pressure therapy device. Moreover, the methods/systems/devices/apparatus can provide improvements in the technological field of automated management, monitoring and/or treatment of respiratory conditions, including, for example, SDB-comorbid insomnia.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7. BRIEF DESCRIPTION OF THE DRAWINGS

The present technology is illustrated by way of example, and not by way of limitation, in the figures of the accompanying drawings, in which like reference numerals refer to similar elements including:

7.1 Treatment Systems

FIG. 1 shows a treatment system including a patient 1000 wearing a patient interface 3000, in the form of a full-face mask, receiving a supply of air at positive pressure from a RPT device 4000. Air from the RPT device 4000 is humidified in a humidifier 5000, and passes along an air circuit 4170 to the patient 1000.

7.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

7.3 Patient Interface

FIG. 3 shows a patient interface in the form of a nasal mask in accordance with one form of the present technology.

7.4 RPT Device

7.5 Humidifier

Figure 5:
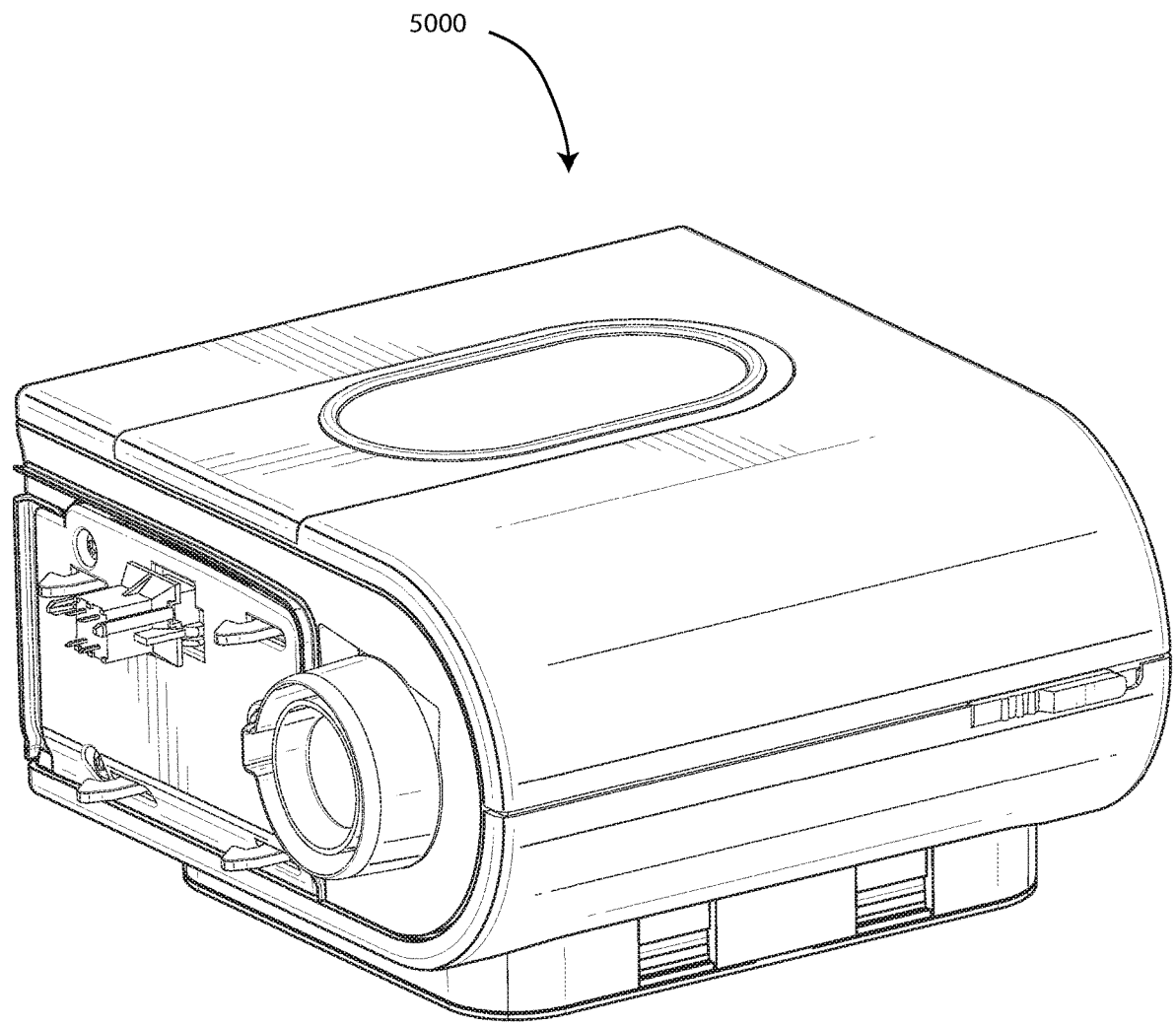

FIG. 5 shows an isometric view of a humidifier in accordance with one form of the present technology.

7.6 Breathing Waveforms

Figure 6A:
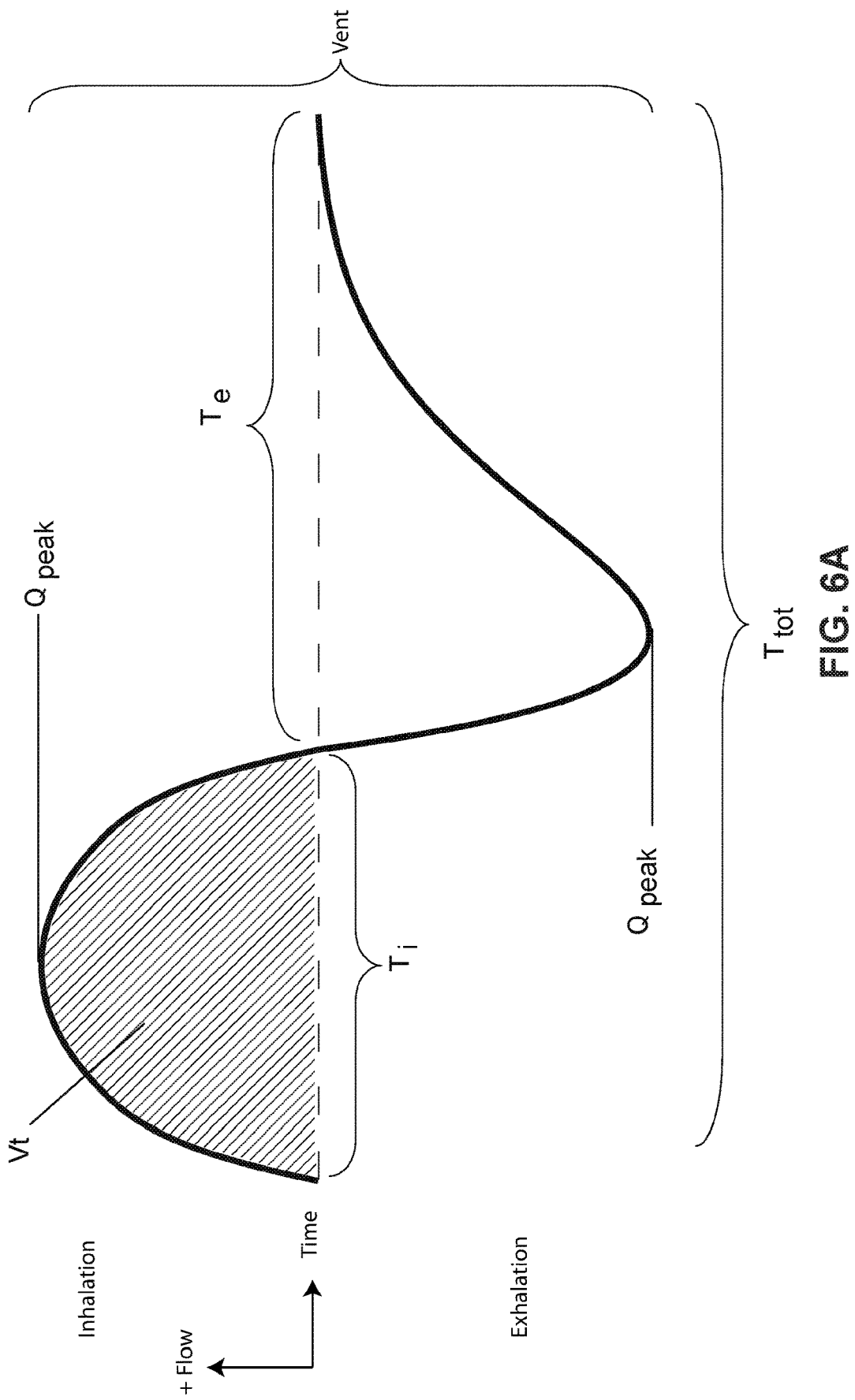

FIG. 6A shows a model typical breath waveform of a person while sleeping.

Figure 6B:
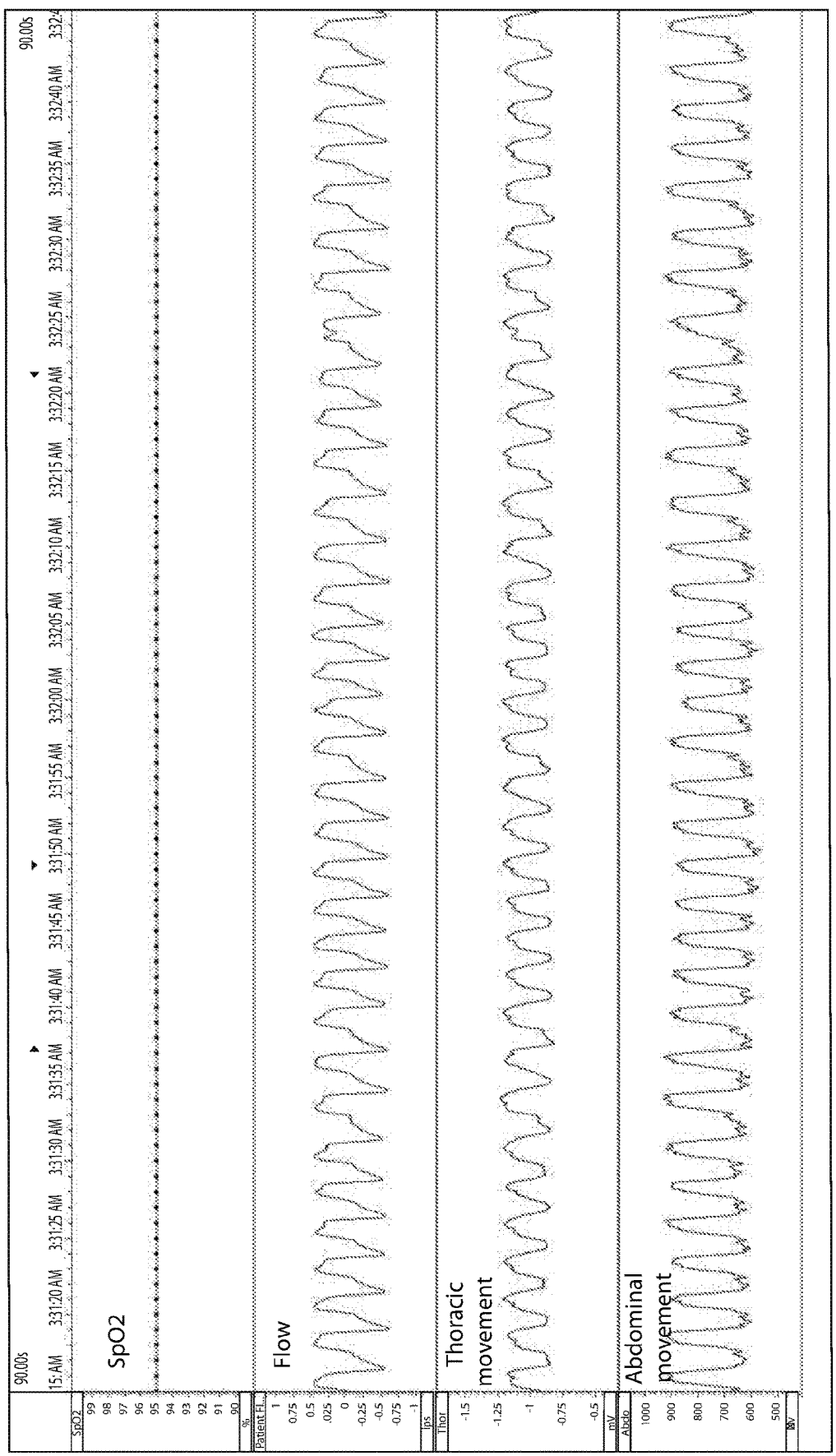

FIG. 6B shows a patient during non-REM sleep breathing normally over a period of about ninety seconds.

Figure 6C:
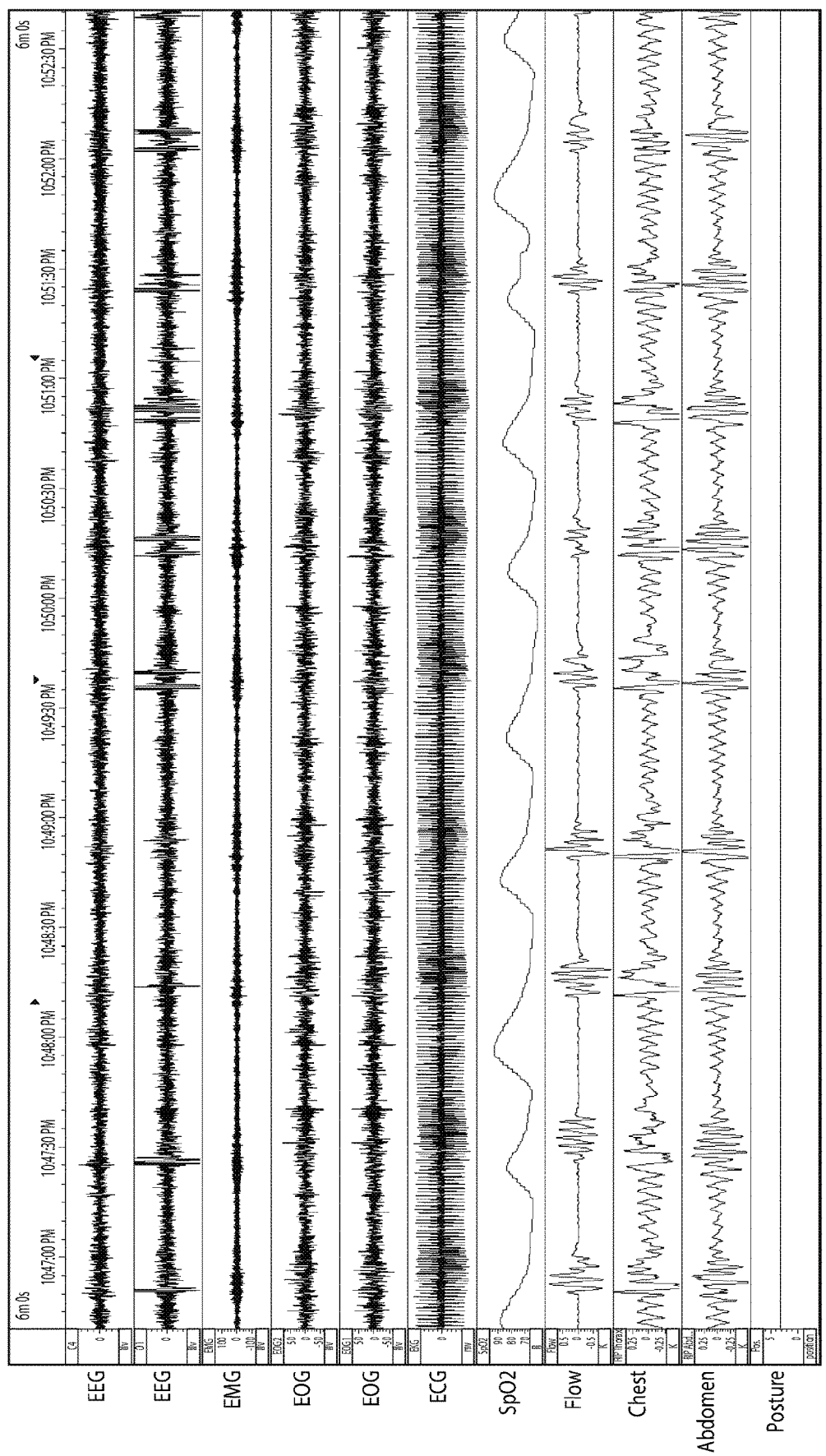

FIG. 6C shows polysomnography of a patient before treatment.

Figure 6D:
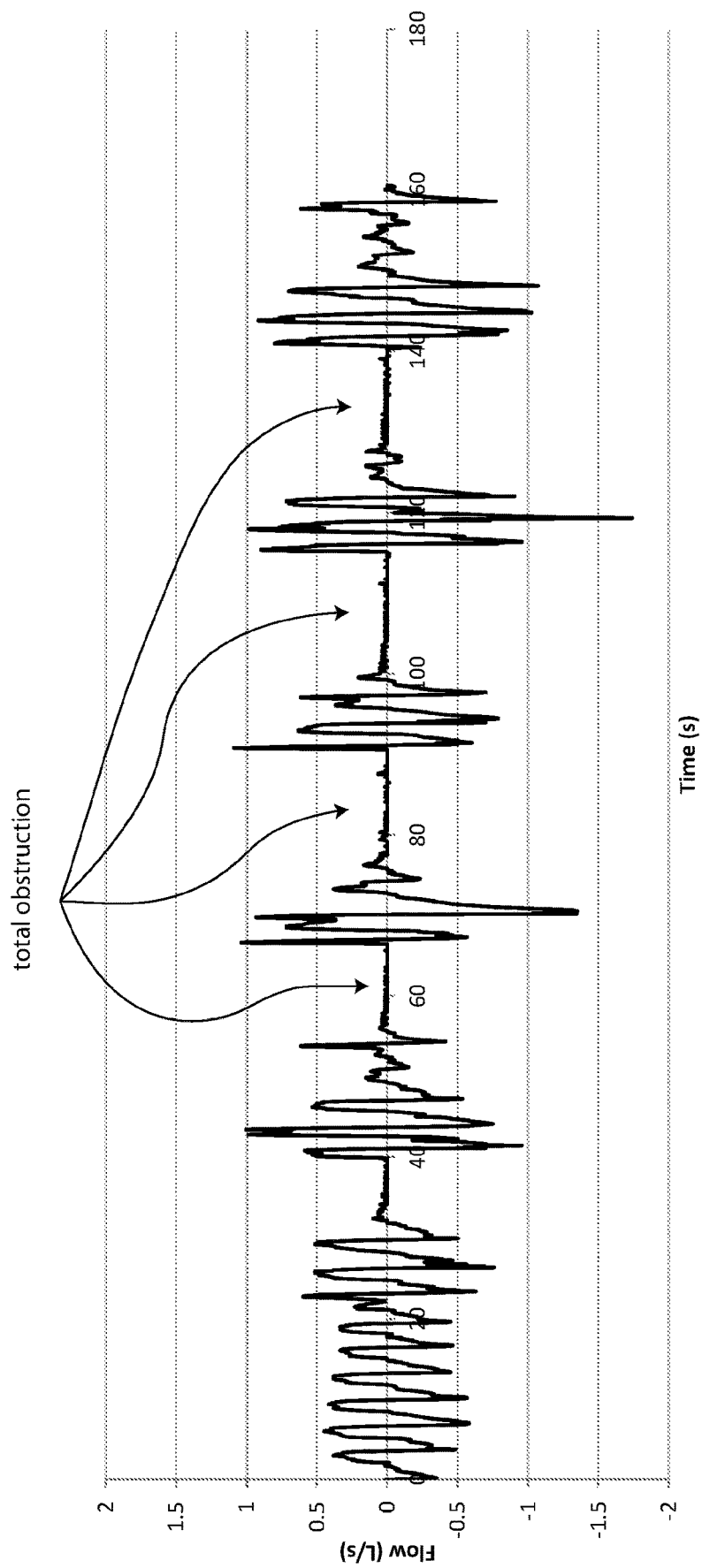

FIG. 6D shows patient flow data where the patient is experiencing a series of total obstructive apneas.

Figure 6E:
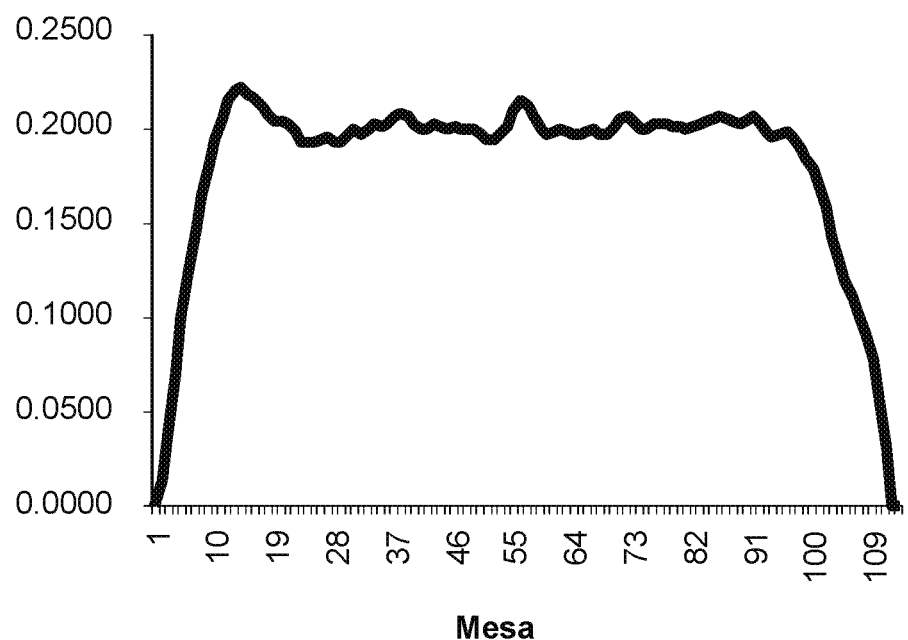

FIG. 6E shows a scaled inspiratory portion of a breath where the patient is experiencing low frequency inspiratory snore.

Figure 6F:
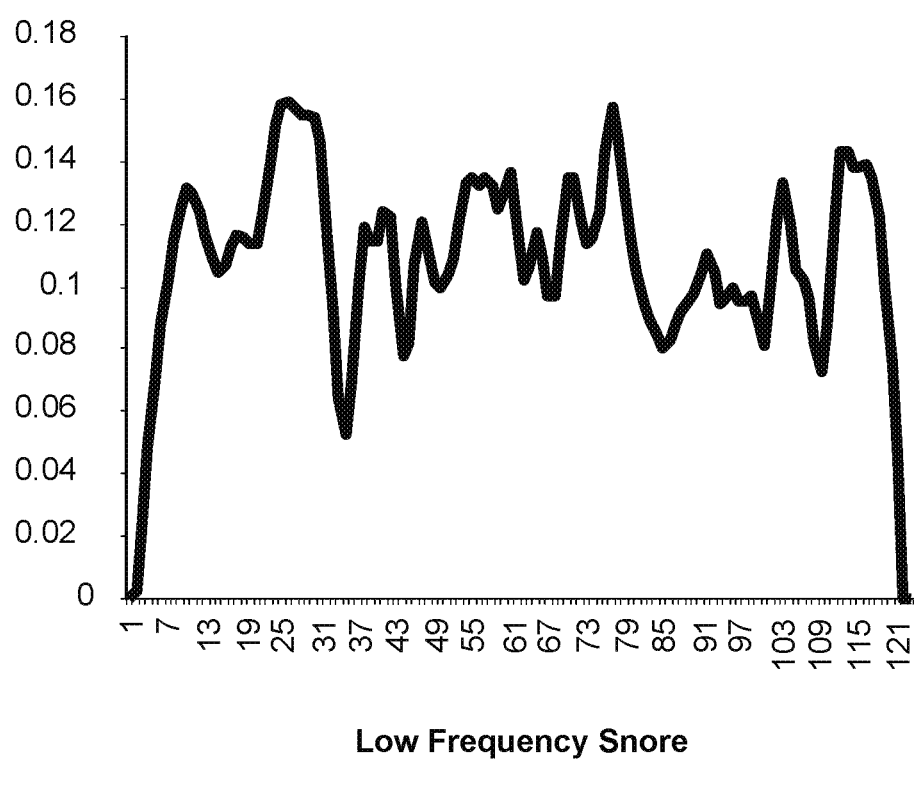

FIG. 6F shows a scaled inspiratory portion of a breath where the patient is experiencing an example of ordinary or "mesa" flattened inspiratory flow limitation.

Figure 6G:
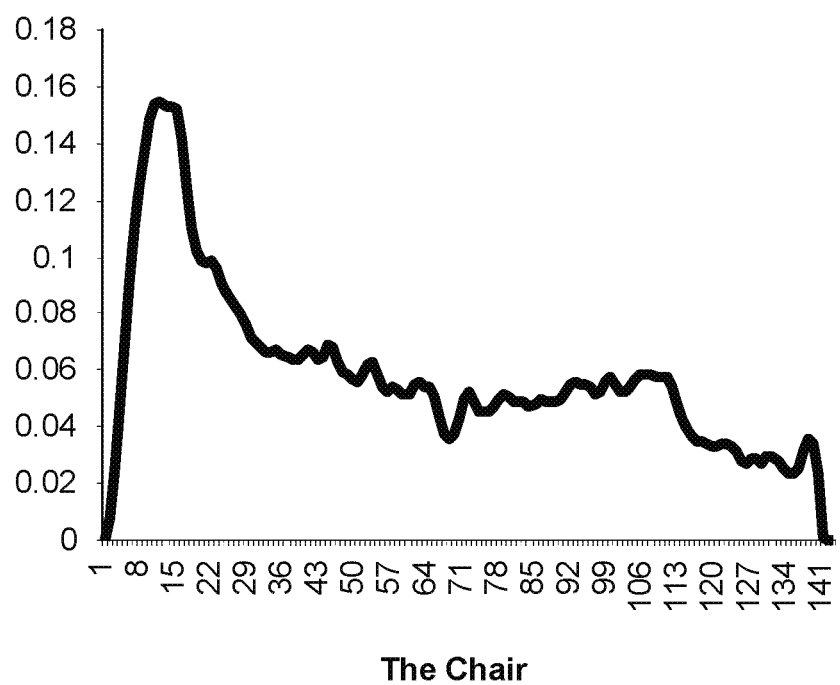

FIG. 6G shows a scaled inspiratory portion of a breath where the patient is experiencing an example of "chair" inspiratory flow limitation.

Figure 6H:
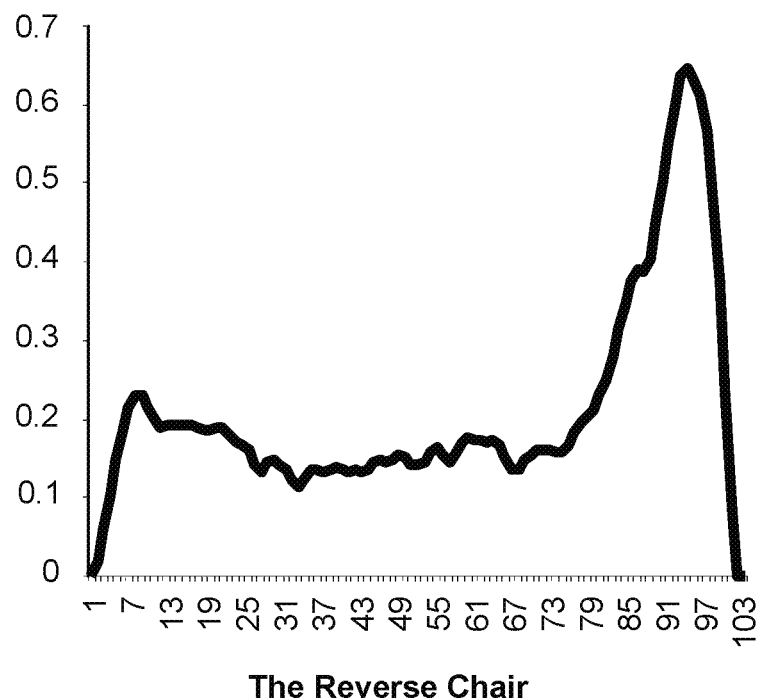

FIG. 6H shows a scaled inspiratory portion of a breath where the patient is experiencing an example of "reverse chair" inspiratory flow limitation.

Figure 6I:
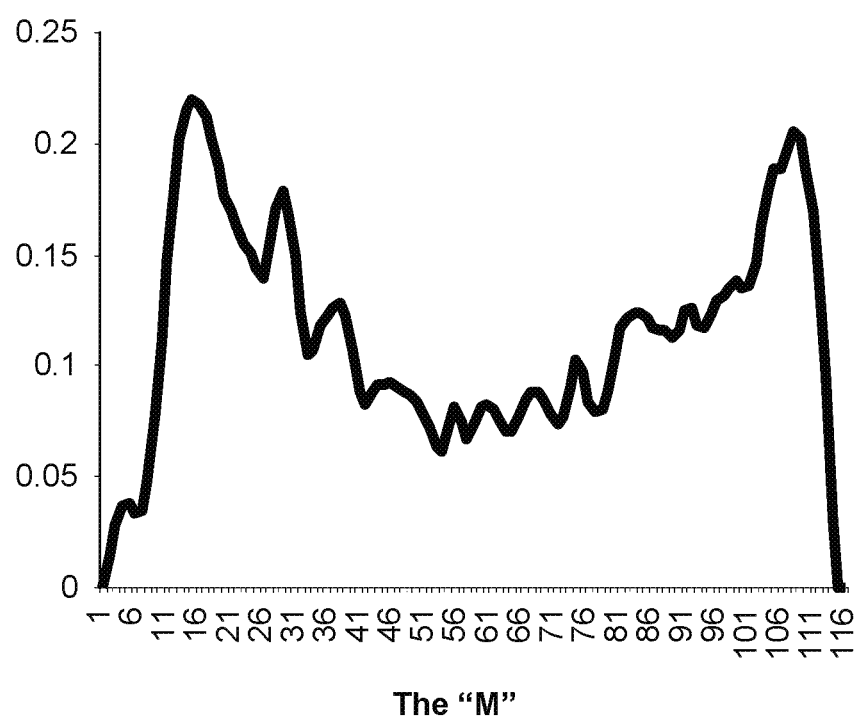

FIG. 6I shows a scaled inspiratory portion of a breath where the patient is experiencing an example of "M-shaped" inspiratory flow limitation.

Figure 6J:
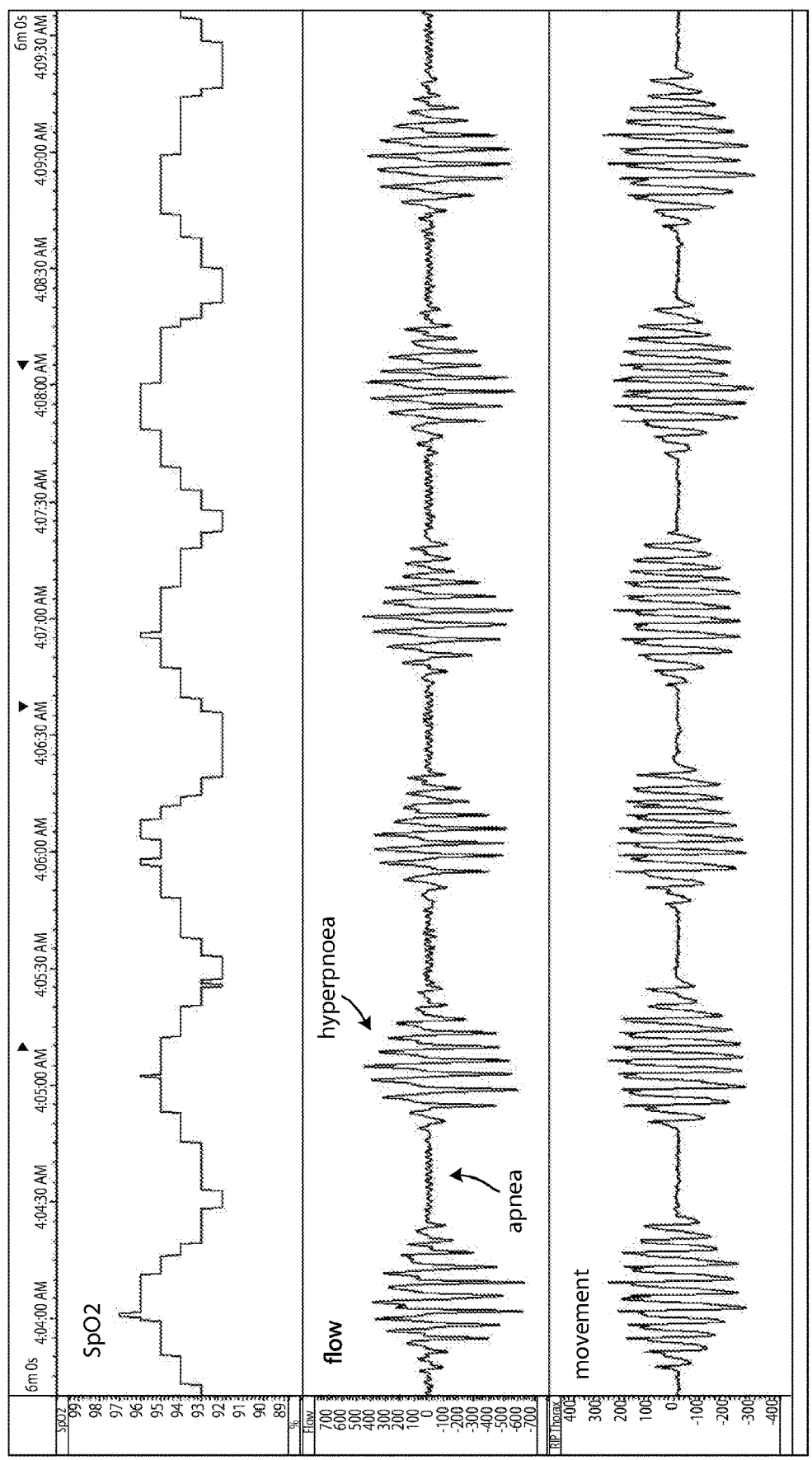

FIG. 6J shows patient data from a patient with Cheyne-Stokes respiration.

7.7 Respiratory Pressure Therapy Modes

Figure 1:
Figure 2:
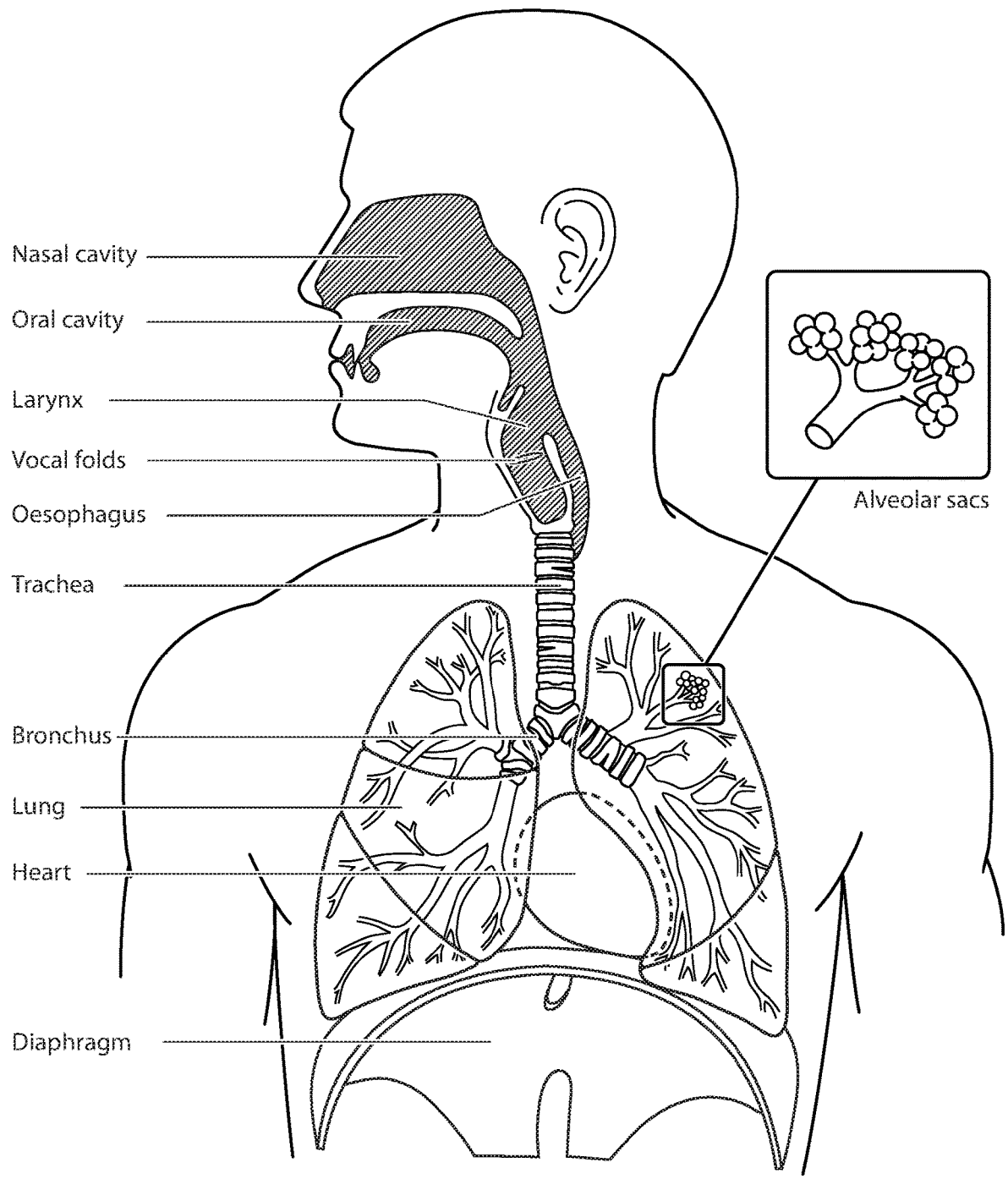
Figure 3:
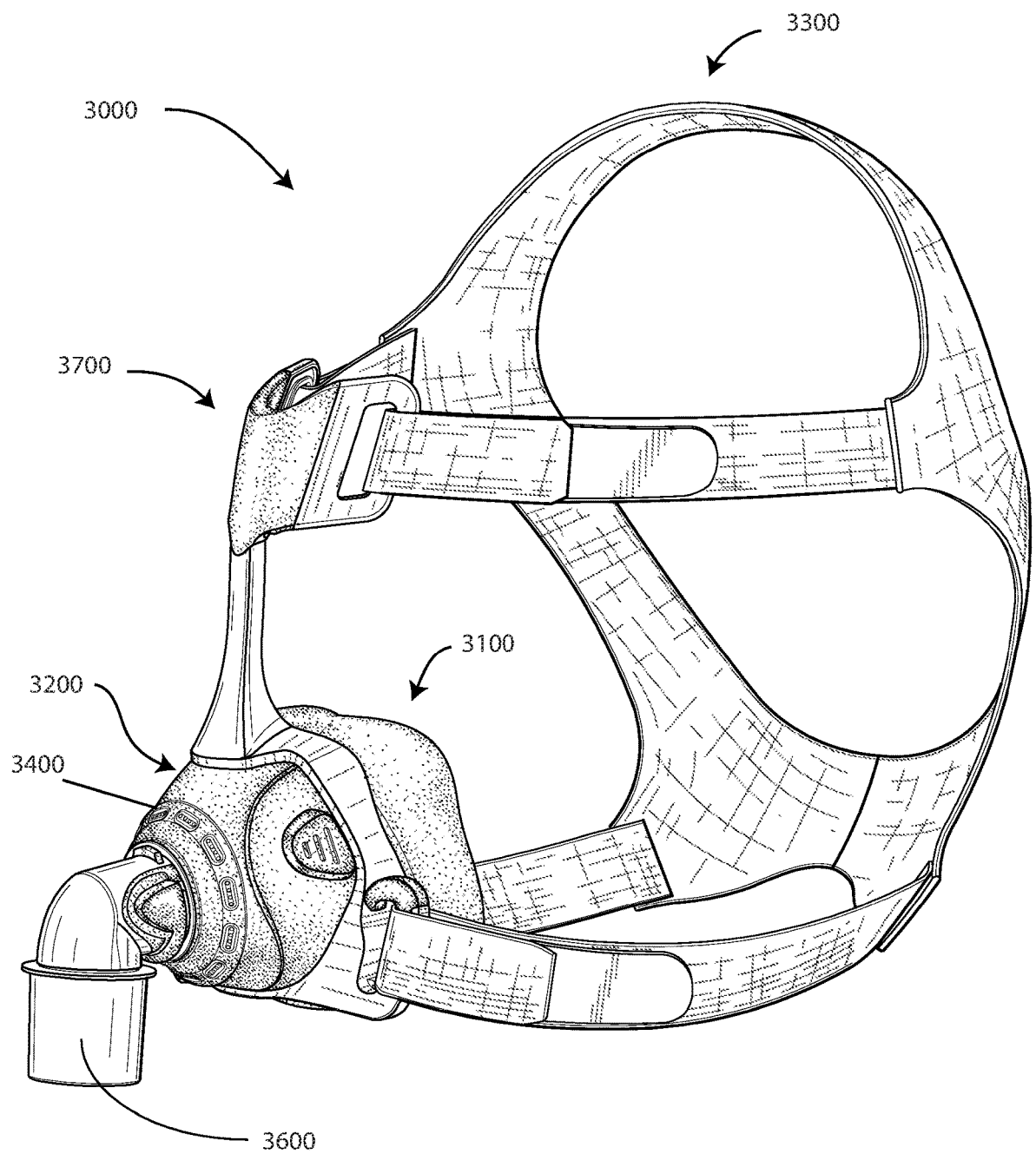
Figure 4A:
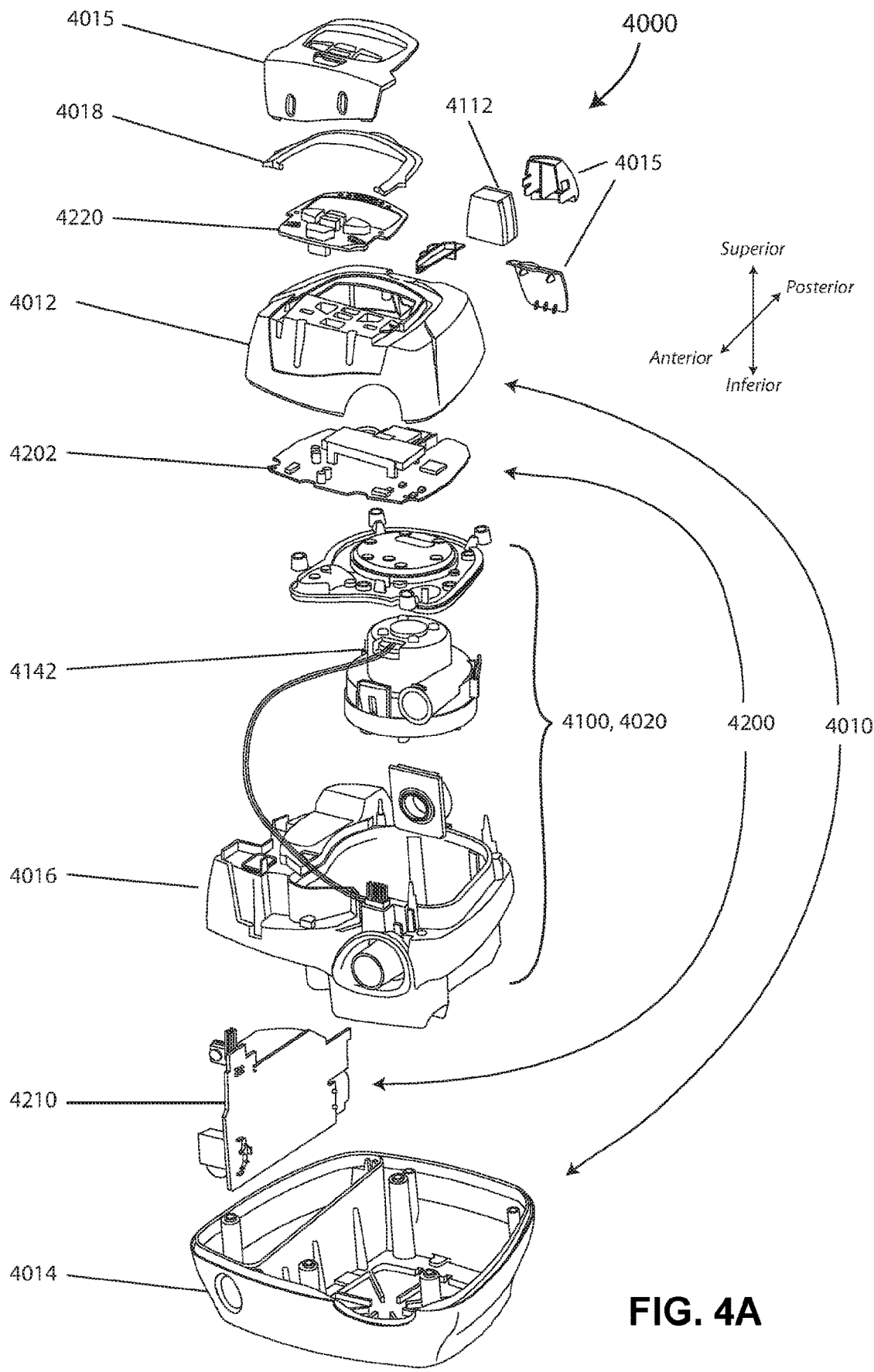
FIG. 4A shows a RPT device in accordance with one form of the present technology.
Figure 4B:
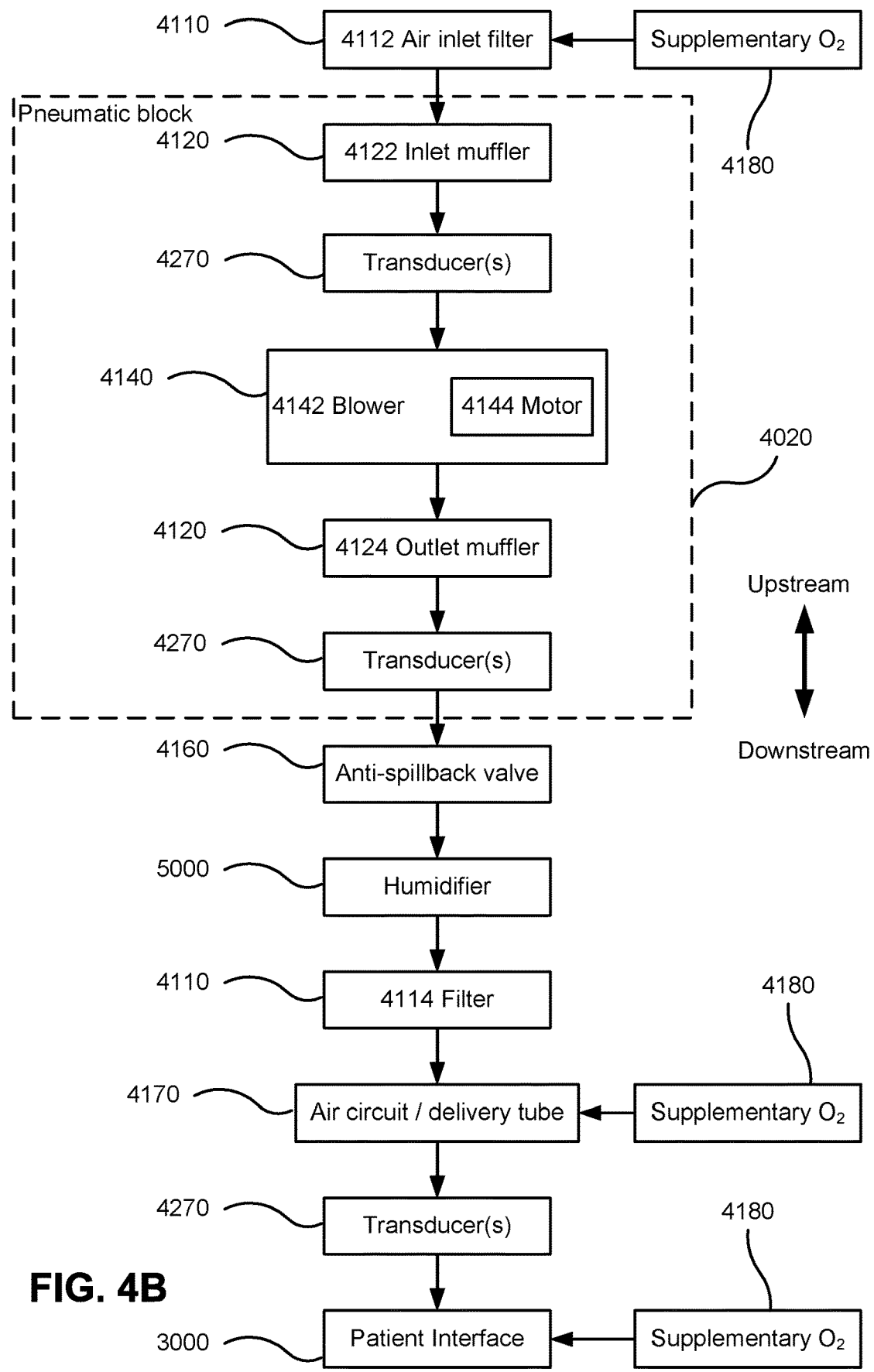
FIG. 4B is a schematic diagram of the pneumatic path of a RPT device in accordance with one form of the present technology. The directions of upstream and downstream are indicated.
Figure 4C:
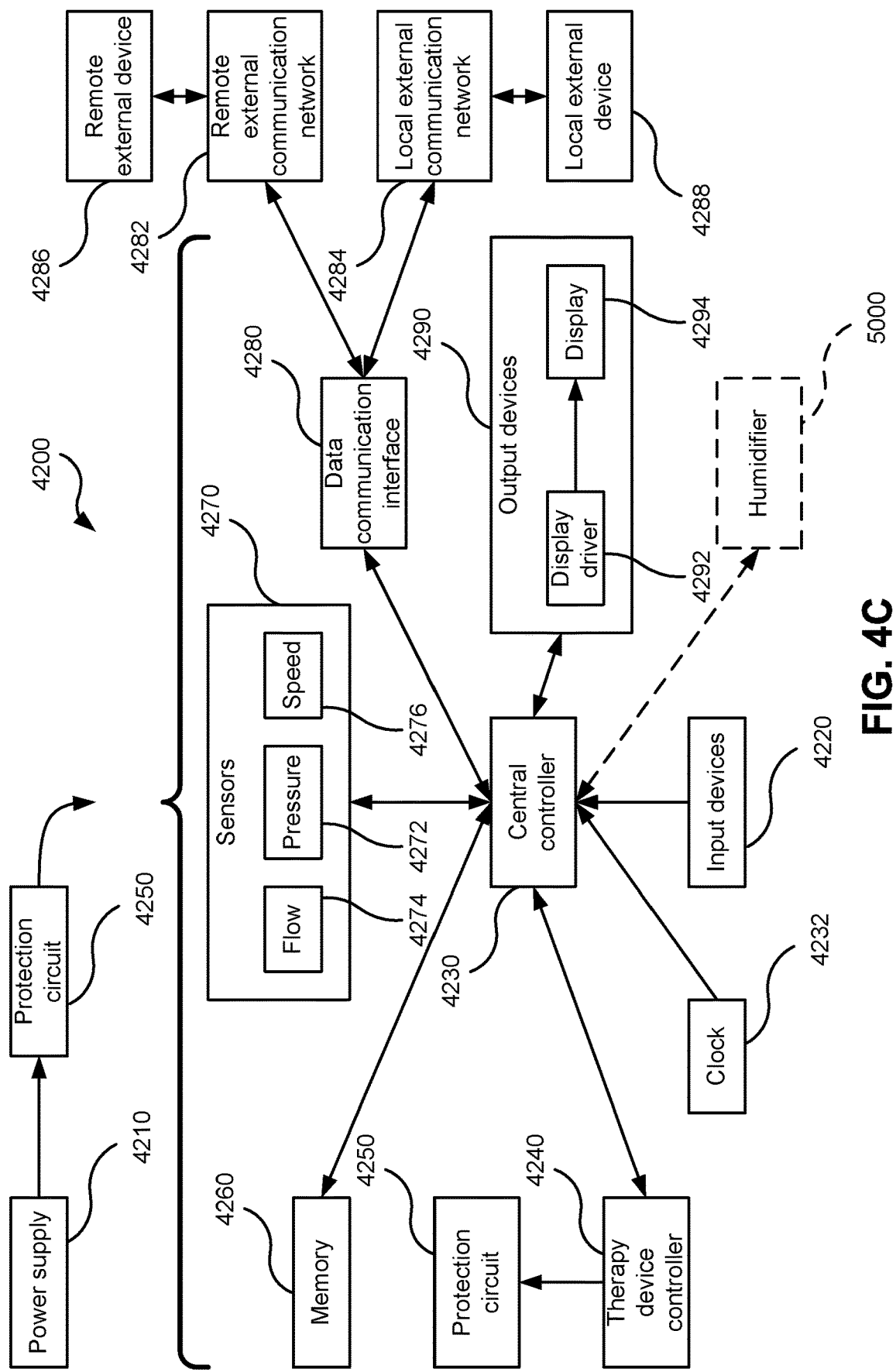
FIG. 4C is a schematic diagram of the electrical components of a RPT device in accordance with one form of the present technology.
Figure 4D:
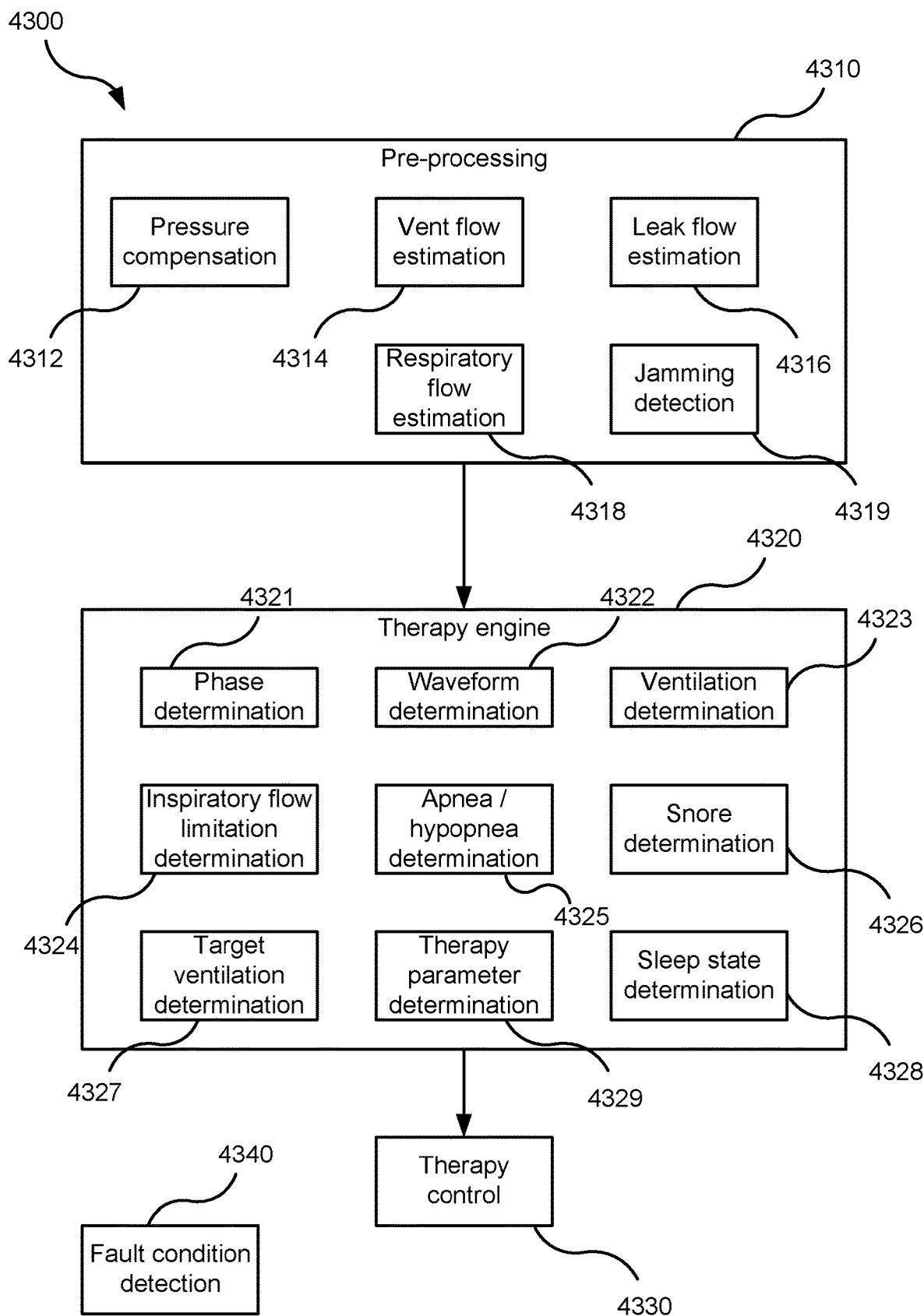
FIG. 4D is a schematic diagram of the algorithms implemented in a RPT device in accordance with one form of the present technology. In this figure, arrows with solid lines indicate an actual flow of information, for example via an electronic signal.
Figure 7:
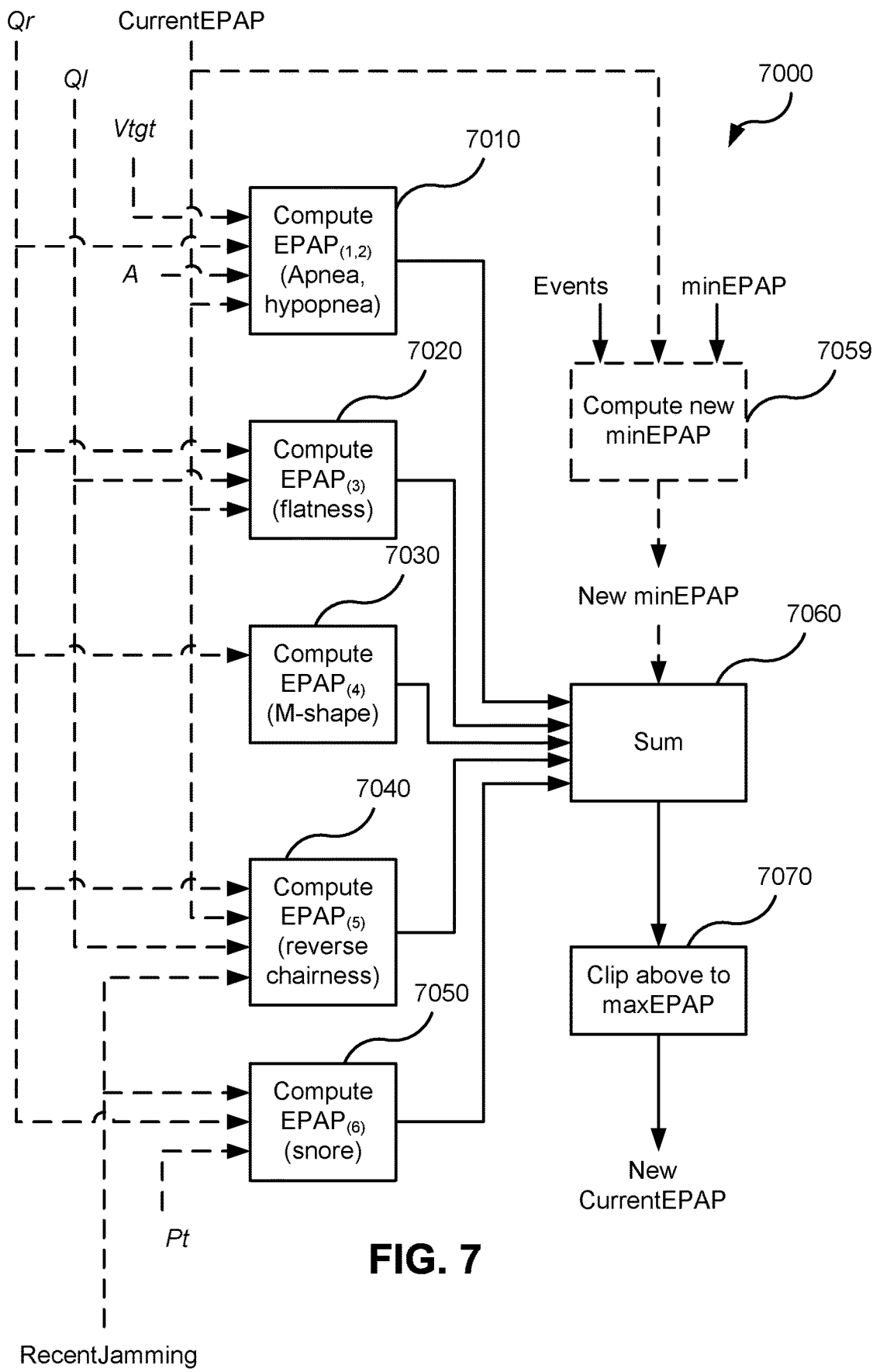

FIG. 7 is flow chart illustrating a method of computing a new value of EPAP in one form of the RPT device of FIG. 4A.

7.8 Pressure Waveforms

Figure 8:
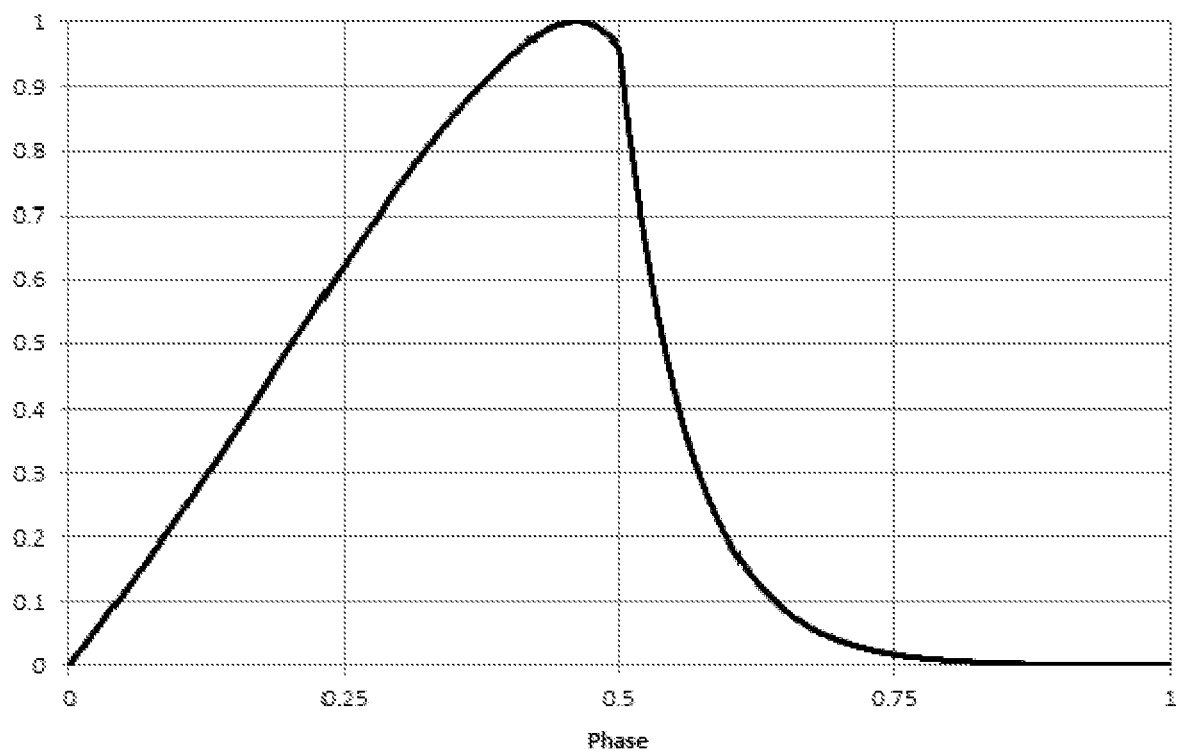

FIG. 8 illustrates an example "smooth and comfortable" treatment pressure waveform template as a function of phase in accordance with one form of the present technology.

Figure 9:
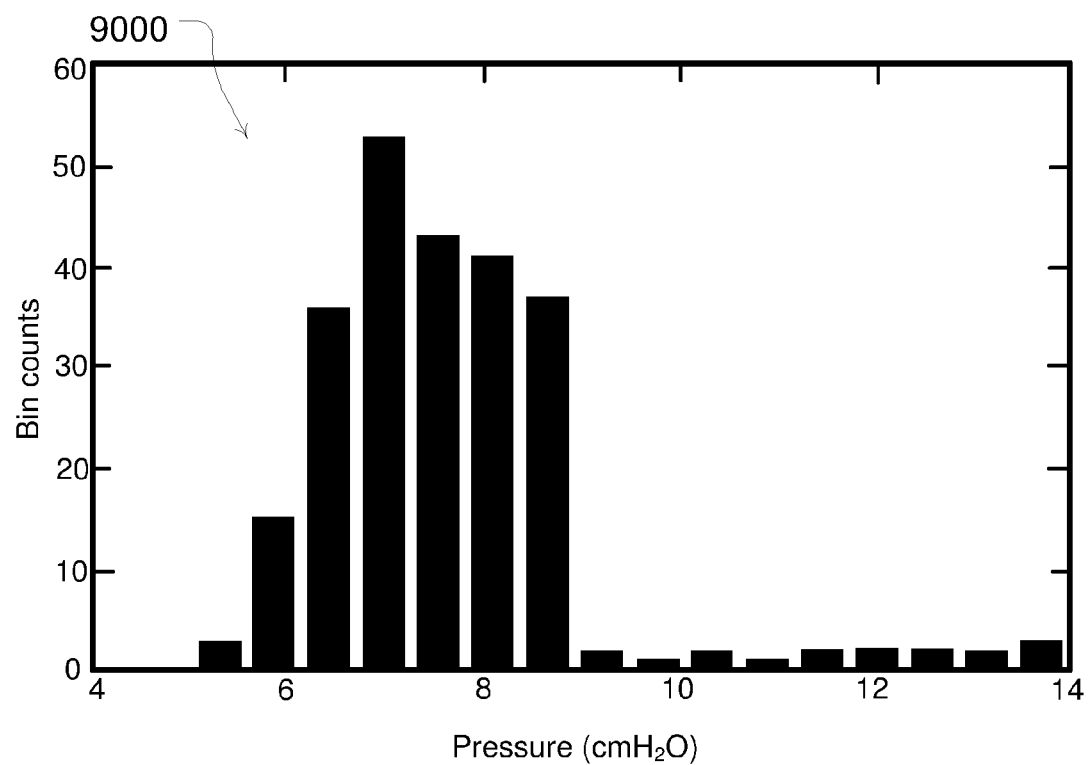

FIG. 9 contains a histogram of EPAP values at which EPAP was incremented during an analysis interval of 60 minutes of auto-titration of EPAP.

Figure 10:
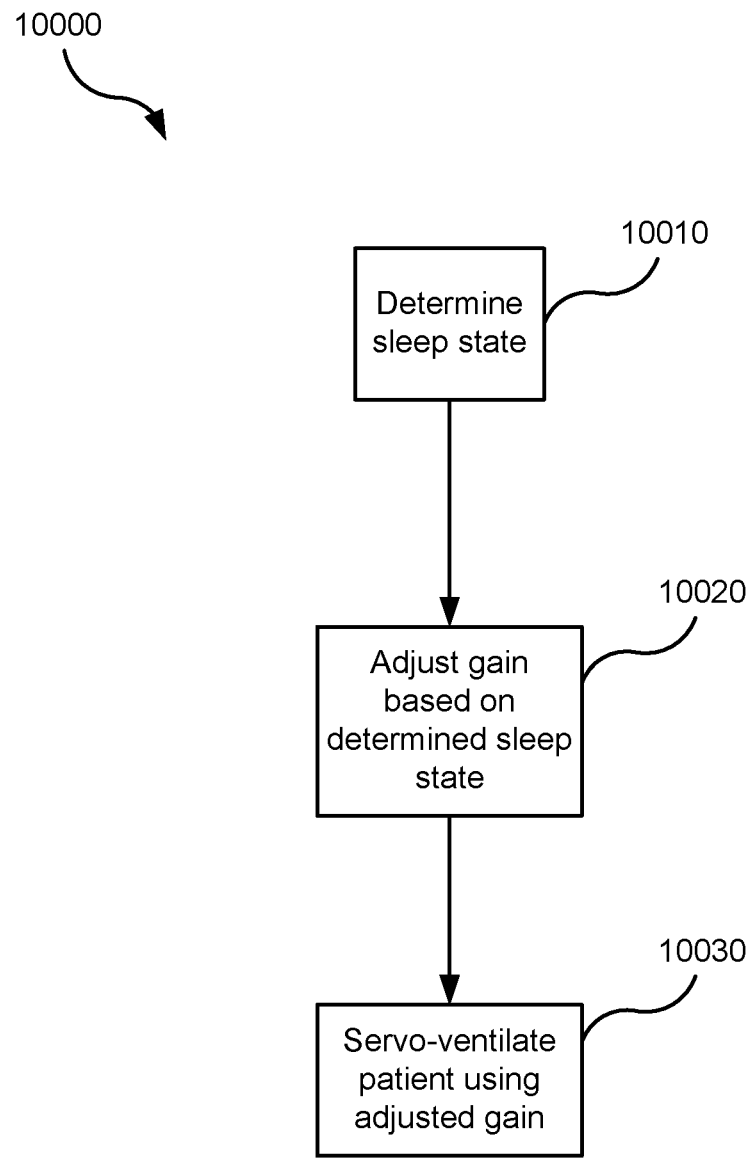

FIG. 10 illustrates a control methodology for adjusting a servo-ventilation control gain based on determined sleep state such as for an RPT device.

Figure 11:
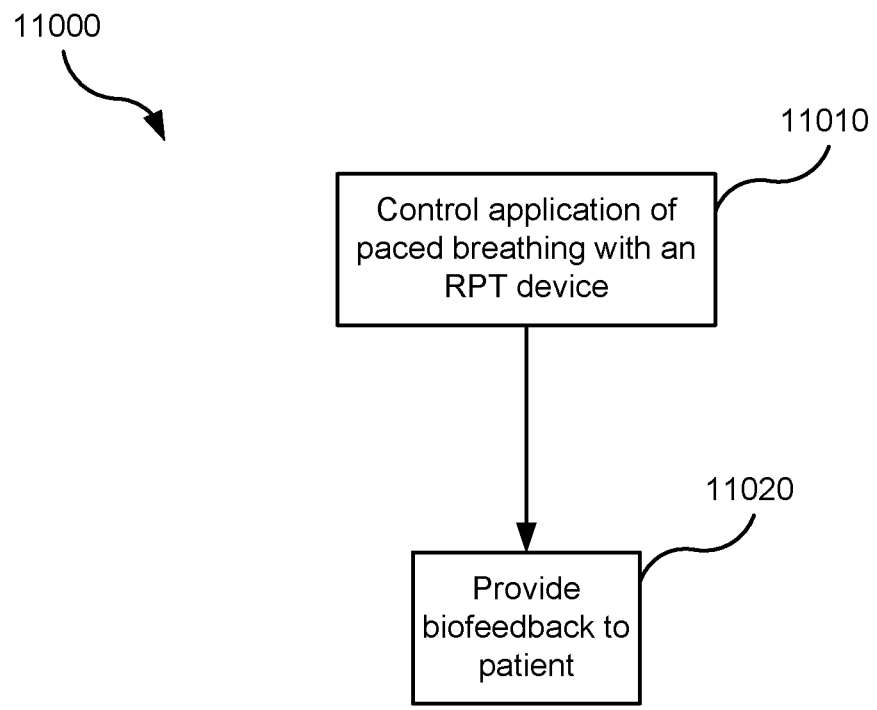

FIG. 11 illustrates an example control methodology for paced breathing by an RPT device with biofeedback.

8. DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

8.1 Therapy

In one form, the present technology comprises a method for treating insomnia, comprising the step of applying positive pressure to the entrance of the airways of a patient 1000.

8.2 Treatment Systems

In one form, the present technology comprises an apparatus or device for treating insomnia. The apparatus or device may comprise a RPT device 4000 for supplying pressurised air to the patient 1000 via an air circuit 4170 to a patient interface 3000.

8.3 Patient Interface

A non-invasive patient interface 3000 in accordance with one form of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

8.4 RPT Device

An RPT device 4000 in accordance with one form of the present technology comprises mechanical and pneumatic components 4100, electrical components 4200 and is configured to execute one or more algorithms 4300. The RPT device has an external housing 4010, possibly formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g. an inlet air filter 4112, an inlet muffler 4122, a pressure generator 4140 capable of supplying air at positive pressure (e.g. a blower 4142), an outlet muffler 4124 and one or more transducers 4270, such as pressure sensors 4272 and flow sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

8.4.1 RPT Device Mechanical & Pneumatic Components

An RPT device may comprise one or more of the following components in an integral unit. In an alternative form, one or more of the following components may be located as respective separate units.

8.4.1.1 Air Filter(s)

A RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

8.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

8.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein in their entirety: U.S. Pat. Nos. 7,866,944; 8,638,014; 8,636,479; and PCT patent application publication number WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

8.4.1.4 Transducer(s)

Transducers may be internal of the RPT device, or external of the RPT device. External transducers may be located for example on or form part of the air circuit, e.g. the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

8.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate such as a total flow rate Qt from the flow rate sensor 4274 is received by the central controller 4230.

8.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

8.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

8.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

8.4.1.6 Air Circuit

An air circuit 4170 in accordance with one form of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

8.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

8.4.2 RPT Device Electrical Components

8.4.2.1 Power Supply

A power supply 4210 may be located internal or external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

8.4.2.2 Input Devices

In one form of the present technology, a RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

8.4.2.3 Central Controller

In one form of the present technology, the central controller 4230 is one or a plurality of processors suitable to control a RPT device 4000.

Suitable processors may include an x86 INTEL processor, a processor based on ARM Cortex-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280, and humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with a RPT device 4000. However, in some forms of the present technology, some methodologies may be performed by a remotely located device. For example, the remotely located device may determine control settings for a ventilator or detect respiratory related events by analysis of stored data such as from any of the sensors described herein.

8.4.2.4 Clock

The RPT device 4000 may include a clock 4232 that is connected to the central controller 4230.

8.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

8.4.2.6 Protection Circuits

The one or more protection circuits 4250 in accordance with the present technology may comprise an electrical protection circuit, a temperature and/or pressure safety circuit.

8.4.2.7 Memory

In accordance with one form of the present technology the RPT device 4000 includes memory 4260, preferably non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which are stored computer program instructions expressing the one or more methodologies described herein, such as the one or more algorithms 4300.

8.4.2.8 Data Communication Systems

In one preferred form of the present technology, a data communication interface 4280 is provided, and is connected to the central controller 4230. Data communication interface 4280 may be connectable to remote external communication network 4282 and/or a local external communication network 4284. Remote external communication network 4282 may be connectable to remote external device 4286. Local external communication network 4284 may be connectable to local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

The local external device 4288 may be a personal computer, "smartphone", tablet computer, "smart watch", or remote control.

8.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

8.4.2.9.1 Display Driver

A display driver 4292 receives as an input the characters, symbols, or images intended for display on the display 4294, and converts them to commands that cause the display 4294 to display those characters, symbols, or images.

8.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

8.4.3 RPT Device Algorithms

8.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the unintentional leak flow rate Ql.

In various forms of the present technology, the pre-processing module 4310 comprises one or more of the following algorithms: pressure compensation 4312, vent flow rate estimation 4314, leak flow rate estimation 4316, respiratory flow rate estimation 4318, and jamming detection 4319.

8.4.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

8.4.3.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

8.4.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate, Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and pressure, Pm.

8.4.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

8.4.3.1.5 Jamming Detection

When the leak has recently changed and the leak flow rate estimation algorithm 4316 has not fully compensated for the change, a state designated as "jamming" exists. In the jamming state, the respiratory flow rate baseline is usually incorrect to some degree, which distorts flow shapes and affects the detection of flow limitation. For example, if the respiratory flow rate baseline is above the true level, respiratory flow rate in late expiration will be positive and thus be taken as early inspiratory flow; if this is expiratory pause flow, the true start of inspiration may be taken as the increase after the flat portion of a reverse chair waveform. Hence a fuzzy truth variable, RecentJamming, which represents the extent to which jamming, i.e. uncompensated leak, has recently existed, is calculated by the jamming detection algorithm 4319.

In the jamming detection algorithm 4319, an instantaneous jamming fuzzy truth variable J is calculated as the fuzzy extent to which the absolute magnitude of the respiratory flow rate Qr has been large for longer than expected. The fuzzy extent $A_I$ to which the respiratory flow rate has been positive for longer than expected is calculated from the time $t_{ZI}$ since the last positive-going zero crossing of the respiratory flow rate Qr, and the inspiratory duration Ti, using the following fuzzy membership function:

$$A_I = \text{FuzzyMember}(t_{ZI}, Ti, 0, 2*Ti, 1) \quad (1)$$

The fuzzy extent $B_I$ to which the airflow rate is large and positive is calculated from the respiratory flow rate Qr using following the fuzzy membership function:

$$B_I = \text{FuzzyMember}(Qr, 0, 0, 0.5, 1) \quad (2)$$

The fuzzy extent $I_I$ to which the leak has suddenly increased is calculated as the fuzzy "and" of the fuzzy truth variables $A_I$ and $B_I$.

Precisely symmetrical calculations are performed for expiration, deriving $I_E$ as the fuzzy extent to which the leak has suddenly decreased. The fuzzy extent $A_E$ to which the airflow rate has been negative for longer than expected is calculated from the time $t_{ZE}$ since the last negative-going zero crossing of the respiratory flow rate Qr, and the expiratory duration Te, using the fuzzy membership function in equation (1). The fuzzy extent $B_E$ to which the airflow rate is large and negative is calculated from the negative of the respiratory flow rate Qr rate using the fuzzy membership function in equation (2), and $I_E$ is calculated as the fuzzy "and" of the fuzzy truth variables $A_E$ and $B_E$. The instantaneous jamming index J is calculated as the fuzzy "or" of the fuzzy truth variables $I_I$ and $I_E$.

If the instantaneous jamming value J is larger than the recent peak value of J, then RecentJamming is set to the instantaneous jamming value J. Otherwise, RecentJamming is set to the instantaneous jamming value J, low pass filtered with a time constant of 10 seconds.

8.4.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, target ventilation determination 4327, sleep state determination 4328, and therapy parameter determination 4329.

8.4.3.2.1 Phase Determination

In one form of the present technology, the RPT device 4000 does not determine phase.

In one form of the present technology, a phase determination algorithm 4321 receives as an input a signal indicative of respiratory flow, Qr, and provides as an output a phase Φ of a current breathing cycle of a patient 1000.

In some forms, known as discrete phase determination, the phase output Φ is a discrete variable. One implementation of discrete phase determination provides a bi-valued phase output Φ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output Φ is determined to have a discrete value of 0 (thereby "triggering" the RPT device 4000) when the respiratory flow rate Qr has a value that exceeds a threshold, and a discrete value of 0.5 revolutions (thereby "cycling" the RPT device 4000) when the respiratory flow rate Qr has a value that is lower than a threshold. The inhalation time Ti and the exhalation time Te may be respectively obtained by subtracting the cycle time from the trigger time, and the following trigger time from the cycle time.

Another implementation of discrete phase determination provides a tri-valued phase output $\Phi$ with a value of one of inhalation, mid-inspiratory pause, and exhalation.

In other forms, known as continuous phase determination, the phase output $\Phi$ is a continuous value, for example varying from 0 to 1 revolutions, or 0 to $2\pi$ radians. RPT devices 4000 that perform continuous phase determination may trigger and cycle when the continuous phase reaches 0 and 0.5 revolutions, respectively. In one implementation of continuous phase determination, a continuous value of phase $\Phi$ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow is zero and increasing fast then the phase is 0 revolutions.
2. If the respiratory flow is large positive and steady then the phase is 0.25 revolutions.
3. If the respiratory flow is zero and falling fast, then the phase is 0.5 revolutions.
4. If the respiratory flow is large negative and steady then the phase is 0.75 revolutions.
5. If the respiratory flow is zero and steady and the 5-second low-pass filtered absolute value of the respiratory flow is large then the phase is 0.9 revolutions.
6. If the respiratory flow is positive and the phase is expiratory, then the phase is 0 revolutions.
7. If the respiratory flow is negative and the phase is inspiratory, then the phase is 0.5 revolutions.
8. If the 5-second low-pass filtered absolute value of the respiratory flow is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

Once the phase $\Phi$ has been estimated, whether discrete or continuous, the inhalation time Ti and the exhalation time Te may be computed as the respective durations of the intervals between the phase reaching 0 and the phase reaching 0.5, and the phase reaching 0.5 and the phase returning to 0.

In another implementation of continuous phase determination, the inhalation time Ti and the exhalation time Te are first estimated from the respiratory flow rate Qr, e.g. by threshold comparison as described above. The phase $\Phi$ is then determined as the half the proportion of the inhalation time Ti that has elapsed since the previous trigger instant, or 0.5 revolutions plus half the proportion of the exhalation time Te that has elapsed since the previous cycle instant (whichever was more recent).

8.4.3.2.2 Waveform Determination

In some forms of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase $\Phi$ of a respiratory cycle of a patient according to a predetermined waveform template $\Pi(\Phi)$.

In such form of the present technology, a waveform determination algorithm 4322 provides a waveform template $\Pi(\Phi)$ with values in the range [0, 1] on the domain of phase values $\Phi$ provided by the phase determination algorithm 4321. The waveform template $\Pi(\Phi)$ is used by the therapy parameter determination algorithm 4329.

The waveform template $\Pi(\Phi)$ may be provided as a lookup table of values H as a function of phase values $\Phi$. This approach is particularly suitable when the phase determination algorithm 4321 returns discrete values of phase such as 0 for inhalation and 0.5 for exhalation. This approach may also be used when the phase determination algorithm 4321 returns a continuously-valued phase $\Phi$.

In one form, suitable for either discrete or continuously-valued phase, the waveform template $\Pi(\Phi)$ is a square-wave template, having a value of 1 for values of phase up to and including 0.5 revolutions, and a value of 0 for values of phase above 0.5 revolutions. In one form, suitable for continuously-valued phase, the waveform template $\Pi(\Phi)$ comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. A typical waveform template $\Pi(\Phi)$ of this "smooth and comfortable" form is illustrated in FIG. 8.

8.4.3.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate shape is constant.

8.4.3.2.4 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

The algorithm 4324 may compute the metric based on at least one of the following three types of inspiratory flow limitation: flatness, M-shape, and "reverse chairness" (see FIGS. 6E, 6I, and 6H for respective examples).

One example of a method that may be used to implement the inspiratory flow limitation determination algorithm 4324 may be found in commonly owned PCT patent application no. PCT/AU2015/050496, filed 27 Aug. 2015, the entire contents of which are herein incorporated by reference.

8.4.3.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow. The flow rate threshold may be a relatively long-term measure of flow.

In one form, a hypopnea will be said to have been detected when a function of respiratory flow rate Qr falls below a second flow rate threshold for a predetermined period of time. The function may determine a peak flow rate, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

8.4.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow signal rate Qr and provides as an output a metric of the extent to which snoring is present.

The snore determination algorithm 4326 may comprises the step of determining the intensity of the flow rate signal in the range of 30-300 Hz. Further, the snore determination algorithm 4326 may comprise a step of filtering the respiratory flow rate signal Qr to reduce background noise, e.g. the sound of airflow in the system from the blower.

8.4.3.2.7 Determination of Target Ventilation

In one form of the present technology, the central controller 4230 takes as input the measure of current ventilation, Vent, and executes one or more target ventilation determination algorithms 4327 for the determination of a target value Vtgt for the measure of ventilation.

In some forms of the present technology, there is no target ventilation determination algorithm 4327, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4327 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4327, the recent history is of the order of several minutes, but in any case should be longer than the timescale of Cheyne-Stokes waxing and waning cycles. The target ventilation determination algorithm 4327 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

8.4.3.2.8 Determination of Sleep State

In some forms of the present technology, the central controller 4230 executes one or more algorithms 4328 for the determination of sleep state. The sleep state determination algorithm 4328 may monitor and analyse a signal representative of a physiological parameter of the patient to determine sleep state. In some implementations, the physiological parameter is the respiratory flow rate Qr. In one such implementation, the patient is assumed initially to be in an awake state. Sleep onset is detected, and thus the asleep state is determined to have been entered, if one or both of the following conditions are detected in the respiratory flow rate Qr:

- Multiple occurrences of SDB events, such as flow limitation, apnea, hypopnea, or snore, detected as described above, within a first predetermined interval. For example, three or more obstructive apnea or hypopnea events within a two minute interval; or five instances of snore within a 5-breath interval.
- An absence of respiratory disturbances for a second predetermined interval. The second predetermined interval may be in the range 10 to 50 breaths, or 20 to 40 breaths, or 25 to 35 breaths, or from 1 to 10 minutes, 1 to 5 minutes, or 2, 3, 4, 5, 6, 7, 8 or 9 minutes, or some other time limit. To detect an absence of respiratory disturbances, the sleep state determination algorithm 4328 may test for a lack of variation over the second predetermined interval of one or more of the following respiratory variables:
  Tidal volume Vt;
  Inspiratory time Ti;
  Breathing rate;
  Inspiratory peak flow rate Qpeak;
  Expiratory peak flow rate location;
  Time since last breath.

Other methods may be used to implement the sleep state determination algorithm 4328 using the patient's respiratory flow rate Qr. One example may be found in commonly owned PCT patent application no. PCT/AU2010/000894, titled "Detection of Sleep Condition", published as WO 2011/006199, the entire contents of which are herein incorporated by reference.

In other implementations, the physiological parameter from which sleep state is determined is obtained from another sensor. The other sensor may form part of the RPT device transducers 4270, or may be a local external device 4288 that communicates with the RPT device via the local network 4284. In one example, the other sensor is a photoplethysmogram, which provides a pulse oximetry signal. In another example, the other sensor is an actigraph (3D accelerometer), which provides an actimetry (activity) signal. In yet another example, the other sensor is an audio sensor.

8.4.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi) + P_0 \qquad (3)$$

where:
A is the amplitude,
$\Pi(\Phi)$ is the waveform template value (in the range 0 to 1) at the current value $\Phi$ of phase, and
$P_0$ is a base pressure.

If the waveform determination algorithm 4322 provides the waveform template $\Pi(\Phi)$ as a lookup table of values H indexed by phase $\Phi$, the therapy parameter determination algorithm 4329 applies equation (3) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be predetermined or computed by the therapy parameter determination algorithm 4329 depending on the chosen respiratory pressure therapy mode, as described below.

8.4.3.3 Therapy Control Module

The therapy control module 4330 in accordance with one form of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt.

8.4.3.4 Detection of Fault Conditions

In one form of the present technology, the central controller 4230 executes one or more methods for the detection of fault conditions. The fault conditions detected by the one or more methods may include at least one of the following:
Power failure (no power, or insufficient power)
Transducer fault detection
Failure to detect the presence of a component
Operating parameters outside recommended ranges (e.g. pressure, flow, temperature, $PaO_2$)
Failure of a test alarm to generate a detectable alarm signal.

Upon detection of the fault condition, the corresponding algorithm signals the presence of the fault by one or more of the following:
Initiation of an audible, visual &/or kinetic (e.g. vibrating) alarm
Sending a message to an external device
Logging of the incident 8.5 Humidifier In one form of the present technology there is provided a humidifier 5000 (e.g. as shown in FIG. 5) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

8.6 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

FIG. 6B shows a patient during Non-REM sleep breathing normally over a period of about ninety seconds, with about 34 breaths, being treated with APAP, and the mask pressure being about 11 cmH$_2$O. The top channel shows oximetry (SpO$_2$), the scale has a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

FIG. 6C shows polysomnography of a patient before treatment. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus recruitment. The fourth & fifth channels are EOG (electro-oculogram). The sixth channel is an electocardiogram. The seventh channel shows pulse oximetry (SpO$_2$) with repetitive desaturations to below 70% from about 90%. The eighth channel is respiratory airflow using nasal cannula connected to a differential pressure transducer. Repetitive apneas of 25 to 35 seconds alternate with 10 to 15 second bursts of recovery breathing coinciding with EEG arousal and increased EMG activity. The ninth channel shows movement of chest and the tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

FIG. 6D shows patient flow data where the patient is experiencing a series of total obstructive apneas. The duration of the recording is approximately 160 seconds. Flow rates range from about +1 L/s to about −1.5 L/s. Each apnea lasts approximately 10-15 s.

FIG. 6E shows a scaled inspiratory portion of a breath where the patient is experiencing low frequency inspiratory snore.

FIG. 6F shows a scaled inspiratory portion of a breath where the patient is experiencing an example of ordinary or "mesa" flatness inspiratory flow limitation.

FIG. 6G shows a scaled inspiratory portion of a breath where the patient is experiencing an example of "chair" inspiratory flow limitation.

FIG. 6H shows a scaled inspiratory portion of a breath where the patient is experiencing an example of "reverse chair" inspiratory flow limitation.

FIG. 6I shows a scaled inspiratory portion of a breath where the patient is experiencing an example of "M-shaped" inspiratory flow limitation.

FIG. 6J shows patient data from a patient with Cheyne-Stokes respiration. There are three channels: oxygen saturation ($SpO_2$); a signal indicative of flow rate; and thoracic movement. The data span six minutes. The signal representative of flow rate was measured using a pressure sensor connected to a nasal cannula. The patient exhibits apneas of about 22 seconds and hyperpneas of about 38 seconds. The higher frequency low amplitude oscillation during apnea is cardiogenic.

8.7 Respiratory Pressure Therapy Modes

Various respiratory pressure therapy modes may be implemented by the RPT device 4000 depending on the values of the parameters A and $P_0$ in the treatment pressure equation (3) used by the therapy parameter determination algorithm 4329 in one form of the present technology.

8.7.1 CPAP Therapy

In some implementations of this form of the present technology, the amplitude A is identically zero, so the treatment pressure Pt is identically equal to the base pressure $P_0$ throughout the respiratory cycle. Such implementations are generally grouped under the heading of CPAP therapy. In such implementations, there is no need for the therapy engine module 4320 to determine phase Φ or the waveform template Π(Φ).

In CPAP therapy modes, the base pressure $P_0$ may be a constant value that is hard-coded during configuration or manually entered to the RPT device 4000. This alternative is sometimes referred to as constant CPAP therapy. The constant value for the base pressure $P_0$ may be selected for a given patient via a process known as titration. During titration, a clinician typically adjusts the treatment pressure Pt in response to observations of flow limitation, apnea, hypopnea, and snore during a titration session. The titrated base pressure $P_0$ may then be computed as a statistical summary of the treatment pressure Pt during the titration session.

Alternatively, the therapy parameter determination algorithm 4329 may repeatedly compute the base pressure $P_0$ during CPAP therapy. In this alternative, the therapy parameter determination algorithm 4329 repeatedly computes the base pressure $P_0$ as a function of indices or measures of sleep disordered breathing returned by the respective algorithms in the therapy engine module 4320, such as one or more of flow limitation, apnea, hypopnea, and snore. This alternative is sometimes referred to as APAP therapy. Because the continuous computation of the base pressure $P_0$ resembles the manual adjustment of the treatment pressure Pt by a clinician during titration, APAP therapy is also sometimes referred to as auto-titrating CPAP.

8.7.2 Bi-Level Therapy

In other implementations of this form of the present technology, the value of amplitude A in equation (3) may be positive. Such implementations are known as bi-level therapy, because in determining the treatment pressure Pt using equation (3) with positive amplitude A, the therapy parameter determination algorithm 4329 oscillates the treatment pressure Pt between two values or levels in synchrony with the spontaneous respiratory effort of the patient 1000. That is, based on the typical waveform templates Π(Φ) described above, the therapy parameter determination algorithm 4329 increases the treatment pressure Pt to $P_0+A$ (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few $cmH_2O$) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded during configuration or manually entered to the RPT device 4000. Alternatively, the therapy parameter determination algorithm 4329 may repeatedly compute the IPAP and/or the EPAP during CPAP with EPR. In this alternative, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 $cmH_2O$. The predetermined pressure support value is a setting of the RPT device 4000, and may be set for example by hard-coding during configuration of the RPT device 4000 or by manual entry through the input device 4220.

In some forms of pressure support ventilation therapy, known as servo-ventilation, the therapy parameter determination algorithm 4329 takes as input the current measure Vent of ventilation and the target value Vtgt of ventilation provided by the target ventilation determination algorithm 4327 and repeatedly adjusts the parameters of equation (3) to bring the current measure Vent of ventilation towards the target value Vtgt of ventilation. In a form of servo-ventilation known as adaptive servo-ventilation (ASV), which has been used to treat periodic breathing, in particular CSR, the target ventilation Vtgt is computed by the target ventilation determination algorithm 4327 from the typical recent ventilation Vtyp, as described above.

In some forms of servo-ventilation, the therapy parameter determination algorithm 4329 applies a control methodology to repeatedly compute the pressure support A so as to bring the current measure Vent of ventilation towards the target ventilation Vtgt. One such control methodology is Proportional-Integral (PI) control. In one implementation of PI control, suitable for ASV modes in which a target ventilation Vtgt is set to slightly less than the typical recent ventilation Vtyp, the pressure support A is computed as:

$$A = G \int (\text{Vent} - Vtgt) dt \qquad (4)$$

where G is the gain of the PI control. Larger values of gain G can result in positive feedback in the therapy engine module 4320. Smaller values of gain G may permit some residual untreated CSR or other periodic breathing. In some implementations, the gain G is fixed at a predetermined value, such as $-0.4$ cmH$_2$O/(L/min)/sec.

In some implementations of servo-ventilation, the value of the pressure support A computed via equation (4) may be clipped to a range defined as [Amin, Amax]. In such implementations, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax are settings of the RPT device 4000, set for example by hard-coding during configuration of the RPT device 4000 or by manual entry through the input device 4220. A minimum pressure support Amin of 3 cmH$_2$O is of the order of 50% of the pressure support required to perform all the work of breathing of a typical patient in the steady state. A maximum pressure support Amax of 12 cmH$_2$O is approximately double the pressure support required to perform all the work of breathing of a typical patient, and therefore sufficient to support the patient's breathing if they cease making any efforts, but less than a value that would be uncomfortable or dangerous.

In pressure support ventilation therapy modes, the EPAP is the base pressure $P_0$. As with the base pressure $P_0$ in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aim of maintaining airway patency, thereby preventing obstructive apneas throughout the pressure support ventilation therapy, in similar fashion to titration of the base pressure $P_0$ in constant CPAP therapy.

Alternatively, the therapy parameter determination algorithm 4329 may repeatedly compute the EPAP during pressure support ventilation therapy. In such implementations, the therapy parameter determination algorithm 4329 repeatedly computes the EPAP as a function of indices or measures of sleep disordered breathing returned by the respective algorithms in the therapy engine module 4320, such as one or more of flow limitation, apnea, hypopnea, and snore. Because the continuous computation of the EPAP resembles the manual adjustment of the EPAP by a clinician during titration of the EPAP, this process is also sometimes referred to as auto-titration of EPAP, and the therapy mode is known as auto-titrating EPAP pressure support ventilation therapy, or auto-EPAP pressure support ventilation therapy.

Auto-titration of the EPAP for pressure support ventilation therapy for SDB-comorbid insomniacs presents particular difficulties, as such patients can arouse in response to relatively mild SDB events. Having aroused they may find it difficult to re-establish sleep. Thus while occasional mild obstruction or respiratory-event-related arousals (RERAs) may be acceptable in the general population, they are inimical to patients with sleep maintenance insomnia. It is therefore even more important for auto-titration of EPAP for such patients to maintain airway patency, rather than simply reacting to obstructive events. The following section describes an algorithm for the auto-titration of EPAP for pressure support ventilation therapy that is suitable for SDB-comorbid insomnia patients.

8.7.2.1 Auto-Titration of EPAP

In one implementation of auto-titration of EPAP, a number of different features indicative of upper airway obstruction (UAO), if present, cause a rise in the EPAP that is broadly proportional to the severity of the UAO. When no features indicative of UAO are present, the EPAP decays progressively towards a floor pressure limit (sometimes simply "floor pressure") or minimum value minEPAP. This decay tends to minimise the EPAP delivered. At any given time, the EPAP is a balance between the forces tending to make it rise and the tendency to decay. An approximate equilibrium may be reached in which occasional indicators of mild UAO cause upward movements in EPAP which are counterbalanced by the decay that occurs when there are no indicators of UAO.

The EPAP response to the indications of flow limitation is progressive (i.e., more severe flow limitation results in a greater EPAP component compared to the EPAP component due to less severe flow limitation), because with progressively more severe flow limitation the need to respond rapidly to try to prevent an apnea or arousal increases, and also because there is less uncertainty about the presence of flow limitation. Control systems with progressive responses to signals are also almost invariably more stable and generally better behaved than those with large changes in response to small changes in the level of signals. For example, in some versions a progressive response may be a response that is proportional to an indication of flow limitation. However, in some versions the progressive responses need not be strictly related by a constant ratio or gain relative to the indications of flow limitation.

When the therapy parameter determination algorithm 4329 prescribes an increase in EPAP, that increase may not occur instantaneously. Such rises in EPAP may be controlled by the controller 4230 and timed to occur only during what the RPT device 4000 considers to be inspiration. It is believed that rises in EPAP during expiration are more prone to cause arousals than the same rises during inspiration, probably because a rise during inspiration decreases inspiratory work, but a rise during expiration tends to push the patient into the next inspiration. An example of such a technique is disclosed in U.S. Patent Application Publication No. 2011/0203588 A1, the entire contents of which are incorporated herein by reference.

FIG. 7 is a flow chart illustrating a method 7000 of determining a new value of EPAP, CurrentEPAP, as a function of the various measures of UAO computed by the algorithms 4324 (inspiratory flow limitation), 4325 (apneas and hypopneas), and 4326 (snore). The method 7000 may be repeatedly used by the therapy parameter determination algorithm 4329 to auto-titrate the EPAP during pressure support ventilation therapy.

The method 7000 computes five separate components of EPAP above the floor pressure minEPAP: $EPAP_{(1,2)}$ (due to apnea and/or hypopnea) at step 7010, $EPAP_{(3)}$ (due to flatness of inspiratory flow) at step 7020, $EPAP_{(4)}$ (due to M-shaped inspiratory flow) at step 7030, $EPAP_{(5)}$ (due to reverse chairness of inspiratory flow) at step 7040, and $EPAP_{(6)}$ (due to snore) at step 7050. Step 7060 adds these five components to the floor pressure minEPAP. Finally at step 7070, the method 7000 ensures that the resulting new value of CurrentEPAP does not exceed a maximum value maxEPAP. In other words, step 7070 "clips above" the newly computed value of CurrentEPAP to maxEPAP. The method 7000 then concludes.

Each of the steps 7010 to 7050 takes as input, in addition to the corresponding measure(s) of UAO, one or more of the following RPT device variables or signals: the respiratory flow rate Qr, the leak flow rate Ql, the current target ventilation Vtgt, the present value of CurrentEPAP, the amount of pressure support A, the instantaneous treatment pressure Pt, and the recent jamming fuzzy truth variable RecentJamming.

More detail on the steps 7010 to 7050 may be found in the PCT patent application PCT/AU2013/000382, published as WO 2013/152403, the entire contents of which are herein incorporated by reference.

In general, it makes sense to require stronger evidence of UAO for the same rise in EPAP as the current value of EPAP increases, because the potential adverse consequences of raised EPAP increase as the EPAP value increases. These consequences are that the maximum possible pressure support, given a fixed maximum treatment pressure, decreases, and leak becomes more likely. As leak flow rate increases, the level of confidence in the accuracy of the calculated respiratory flow rate waveform decreases, because leak models tend to become increasingly inaccurate as the magnitude of the leak flow rate increases.

In a variation of the method 7000, EPAP, currentEPAP may not be decreased from its present value if the sleep state determination algorithm 4328 determines that the patient is in the asleep state. In such a variation, if the sleep state determination algorithm 4328 determines that the patient is in the asleep state, the new value of currentEPAP after step 7070 is compared with the previous value of currentEPAP, and if it is less, the value of currentEPAP is left unchanged. In this variation, while the patient is determined to be in the asleep state, the EPAP cannot decrease, but only increases or stays the same, to minimise the chance of arousal due to upper-airway resistance in this readily-aroused population.

8.7.2.2 Adjustment of Floor Pressure Limit

In pressure support ventilation therapy, the treatment pressure Pt determined using equation (3) is greater than or equal to the EPAP at all times. In some implementations of pressure support ventilation therapy in which the EPAP is auto-titrated, such as the one described above, the EPAP may be limited to vary within a range bounded below by the minimum value or floor pressure minEPAP and bounded above by the maximum value maxEPAP. This means that the treatment pressure Pt is bounded below by the floor pressure minEPAP which serves as a lower limit to the EPAP pressure. In some such implementations of EPAP auto-titration, the floor pressure minEPAP and the maximum value maxEPAP may be constant values that are hard-coded during configuration or manually entered to the RPT device 4000. Typical constant values for the floor pressure minEPAP and the maximum value maxEPAP are 4 and 15 $cmH_2O$ respectively.

In other implementations of EPAP auto-titration, the floor pressure minEPAP may be repeatedly adjusted depending on events of interest during the EPAP auto-titration. Such a methodology is further illustrated in FIG. 7 with optional floor pressure minEPAP computation process 7059. In some such implementations, the therapy parameter determination algorithm 4329 may repeatedly adjust the floor pressure minEPAP in parallel with the auto-titration of the EPAP such as with the process 7059. In one such implementation, the therapy parameter determination algorithm 4329 repeatedly adjusts the floor pressure minEPAP dependent on the number of events of interest that occur in a predetermined interval Ta. That is, minEPAP is increased by an increment $\Delta$minEPAP if Na or more events of interest occur within an interval of Ta seconds. In one such implementation, an event of interest is an SDB event such as inspiratory flow limitation, apnea, hypopnea, or snore, as determined from the measures of these quantities obtained by the therapy engine module 4320 as described above. In one example of such an implementation, $\Delta$minEPAP is predetermined at 1 $cmH_2O$, Na is 3, and Ta is 2 minutes. In other examples, $\Delta$minEPAP is predetermined at other values in the range 0.2 to 4 $cmH_2O$, or 0.5 to 2 $cmH_2O$. In other examples, Ta is predetermined at other values in the range 30 seconds to 10 minutes, or 1 to 4 minutes.

In other such implementations, the increment $\Delta$minEPAP is not predetermined, but is dependent on the current value of the EPAP. In one such implementation, the increment $\Delta$minEPAP is equal to the EPAP value minus the current value of the floor pressure minEPAP, so that floor pressure minEPAP increases to the current value of the EPAP.

In other implementations of EPAP auto-titration in which the floor pressure minEPAP is repeatedly adjusted, the events of interest are recent increments to the EPAP as a result of the auto-titration of the EPAP. In such implementations, if there have been a predetermined number of increments to the EPAP within a certain time interval, this reflects a situation where an EPAP value below the current EPAP is not sufficient to maintain airway patency, and therefore the floor pressure minEPAP may increase to the current EPAP. In one example of such an implementation, at a time t, the EPAP is 4 $cmH_2O$, and then later on at a time t+3 minutes, the EPAP is 8.5 $cmH_2O$, and there have been 10 increments in the EPAP in the 3-minute interval since the time t. If the threshold for the number of increments is 9 and the threshold for the time interval is 5 minutes, the floor pressure minEPAP would be set to the current EPAP (8.5 $cmH_2O$) because there have been more than 9 increments during an interval of less than 5 minutes.

As additional step to the above implementation, the aggregate increment to the EPAP could also be considered. For example, if the aggregate increment to the EPAP between the times t and t+3 were greater than a threshold, e.g. 3 $cmH_2O$, the floor pressure minEPAP would be set to the current EPAP.

In yet other implementations of EPAP auto-titration in which the floor pressure minEPAP is variable, the therapy parameter determination algorithm 4329 may form a distribution of EPAP values at which EPAP increments occurred over an analysis interval that is long (e.g. 60 minutes) compared to the typical interval between EPAP increments. Based on either parametric or non-parametric statistical analysis of the distribution, the floor pressure minEPAP may be adjusted. FIG. 9 contains an example histogram 9000 representing the distribution of EPAP values at which EPAP increments occurred over the analysis interval, in this example 60 minutes. In this example, the floor pressure minEPAP may be set to 7 cmH$_2$O, which is the mode (peak location) of the histogram. Other statistical extracts of the distribution could be used as the new value of floor pressure minEPAP, e.g. mean, median, etc. Alternatively, the floor pressure minEPAP may be "remembered" from the previous analysis interval, and the new floor pressure minEPAP may be based on the remembered floor pressure as well as the distribution.

The distribution analysis and updating of minEPAP could be repeated at regular intervals throughout the session, e.g. every 60 minutes. The analysis interval may be from 30 to 300 minutes, for example. The interval between distribution analyses and adjustments of the floor pressure minEPAP could be the same as the analysis interval, or longer, or shorter.

In one example, the distribution of EPAP increments is analysed and the floor pressure minEPAP is adjusted after every night of pressure support ventilation therapy. The analysis interval is the complete night, or at least the portions thereof during which the patient was determined to be in the asleep state by the sleep state determination algorithm 4328. Such an example is effectively a night-to-night learning of the "ideal" floor pressure minEPAP for the patient. Such a long analysis interval may provide benefits to the patient in the form of lower leak levels and increased comfort.

In some implementations of EPAP auto-titration with a repeatedly adjusted floor pressure minEPAP, the therapy parameter determination algorithm 4329 ensures the floor pressure minEPAP is always less than or equal to an upper limit minEPAP_max, e.g. 10 cmH$_2$O. In other such implementations, there is no such upper limit on the variable value of the floor pressure minEPAP.

8.7.2.3 Variation of PI Gain Depending on Sleep State

SDB-comorbid insomnia patients may be particularly prone to being unsettled by any therapy changes, given that they are usually in an elevated state of anxiety and stress. Large pressure swings whilst such patients are awake may not be desirable.

Therefore, in some implementations of pressure support ventilation therapy, the gain G of the PI control equation (4) above may be variable depending on the sleep state determined by the sleep state determination algorithm 4328. Such a process 10000 is illustrated in FIG. 10. At 10010, a sleep state is determined such as by sleep state determination algorithm 4328. At 10020 a gain, such as for controlling servo-ventilation, is adjusted based on the determined sleep state. This may be performed by the therapy parameter determination algorithm 4329. At 10030, servo-ventilation is controlled to servo-ventilate the patient with the determined gain such as by the therapy control algorithm 4330. In one such implementation, a fixed, raw value of controller gain $G_0$ is weighted according to sleep state to produce the actual gain G:

$$G = \text{SleepStateWeight} \times G_0 \qquad (5)$$

If the sleep state determination algorithm 4328 determines the patient is in an awake state, the sleep state weight would be close to 0, so the gain G of the servo-control would be relatively low, and the servo-control of pressure support A would be relatively slow-responding. On the other hand, if the sleep state determination algorithm 4328 determines the patient to be asleep, the sleep state weight would be closer to 1, so the gain G of the servo-control would be relatively high, and hence the servo-control of pressure support A would be relatively fast-responding. The transition of the sleep state weight from 0 to 1, and vice versa, may be instantaneous or gradual, e.g. via a linear or exponential function.

8.7.2.4 Acclimatization to Pressure Support Ventilation Therapy

As mentioned above, SDB-comorbid insomniacs are commonly intolerant of conventional respiratory pressure therapy. This is partly because insomnia sufferers are commonly anxious regarding sleep, or anxious in general, and furthermore may not associate their condition with a breathing disorder. Specialised "acclimatization therapy" may therefore be needed to assist the patient to tolerate the respiratory pressure therapy. A previous approach to acclimatization for SDB-comorbid insomnia patients includes desensitization to the patient interface and to the therapy pressure, behavioural therapy to overcome aversive emotional reactions, mental imagery to divert patient attention from patient interface or pressure sensations, and physiological exposure to pressure support ventilation therapy during a daytime sleeping period ("PAP-NAP").

In one form of the present technology, acclimatization therapy comprises a session of "paced breathing". Paced breathing comprises the use of pressure support ventilation to slow down a patient's breathing toward an "optimal" breathing rate in a manner that is sympathetic to the response of the patient such that the therapy is well tolerated. It is established that slow-paced breathing can be calming, particularly in patients who are sympathetically over-active, such as SDB-comorbid insomniacs.

Such a process 11000 is illustrated in FIG. 11. At 11010, an RPT device controls an application of paced breathing for a patient. This may be performed by the therapy parameter determination algorithm 4329 and the therapy control algorithm 4330. At 11020, biofeedback is provided to the patient. This may also be performed by the therapy parameter determination algorithm 4329 and the therapy control algorithm 4330.

For example, a session of paced breathing typically starts with an introductory period of pressure support ventilation therapy as described above, during which the patient's spontaneous inhalation time Ti and exhalation time Te are estimated from the respiratory flow rate Qr as described above. The estimated phase $\Phi$ is used in equation (3) to compute the treatment pressure Pt with a "smooth and comfortable" pressure waveform template $\Pi(\Phi)$ such as that illustrated in FIG. 8.

After the introductory period, the therapy parameter determination algorithm 4329 sets a current interim breathing rate target. The reciprocal of this interim breathing rate target, the target respiratory time tgtTtot, may be partitioned into a target inhalation time tgtTi and a target exhalation time tgtTe in the same proportion as the spontaneous inhalation time Ti and exhalation time Te. Pressure support ventilation therapy is continued using the "smooth and comfortable" pressure waveform template $\Pi(\Phi)$, using phase $\Phi$ estimated as described above, via elapsed time relative to the target inhalation time tgtTi and exhalation time tgtTe. This causes the "smooth and comfortable" treatment pressure Pt to encourage the patient's inhalation time Ti and exhalation time Te to match the target inhalation time tgtTi and the target exhalation time tgtTe. However, the patient's spontaneous respiratory effort sets the trigger and cycle instants, in that the phase $\Phi$ is set to 0.5 (thereby cycling the ventilator) when the respiratory flow falls below a cycle threshold, and reset to 0 (thereby triggering the ventilator) when the respiratory flow rises above a trigger threshold. The cycle threshold is a generally increasing function of flow rate versus time within a breath. Different interim breathing rate targets have different cycle threshold functions, so as to allow easier cycling as the patient's breathing rate tends toward the interim breathing rate target. Similarly, the trigger threshold is a generally decreasing function of flow rate versus time within a breath. Different interim breathing rate targets have different trigger threshold functions, so as to allow easier triggering as the patient's breathing rate tends toward the interim breathing rate target.

As an additional measure to lengthen the patient's respiratory time Ttot and thereby slow down the breathing rate, the pressure support A is increased if the patient's breathing rate is greater than the interim breathing rate target. This tends to cause an increase in tidal volume, and therefore a slowing of breathing rate in order to maintain a constant ventilation. The magnitude of the pressure support increase may be a function of the difference between the interim breathing rate target and the patient's current breathing rate. The interim breathing rate target may be periodically reduced in response to the patient's breathing rate slowing down toward the current interim breathing rate target, until the optimal breathing rate is achieved. One example of an optimal breathing rate is 6 breaths per minute. A sudden increase in spontaneous breathing rate, such as occurs during an arousal, causes the schedule of reduction of interim breathing rate targets to be aborted and the paced breathing to begin again after a predetermined interval.

Some implementations of paced breathing may provide a confirmation signal indicating to the patient when they have achieved the optimal breathing rate, in a manner that is not disturbing to a bed partner. In such implementations, in order to assist the patient in going or returning to sleep, the accompanying non-partner-disturbing confirmation signal may be non-visual and non-acoustic, such as via transient modifications to the treatment pressure Pt. In one example, a barely discernable soft pressure "bump" is added to the treatment pressure Pt at the target inhalation time tgtTi and the target exhalation time tgtTe. Another example is a pressure oscillation delivered within the patient interface 3000 via the air circuit 4170 at a sub-acoustic frequency. Such a pressure oscillation is delivered at an amplitude that is able to be perceived by face mechanoreceptors, but not heard.

Paced breathing may be combined with biofeedback matched to the interim breathing rate target to further improve its effectiveness in slowing breathing. The biofeedback, which could take visual or acoustic form such as calming scene visualisation (e.g. flower unfolding, or backlight with colour shifts) or calming sounds (e.g. wave motion), may further encourage the patient's breathing to slow to the interim breathing rate target. The biofeedback may be provided via a local external device 4288 that communicates with the RPT device 4000 via the local network 4284. A local external device 4288 suitable for this purpose may be a personal computer, "smartphone", tablet computer, projector, "smart watch", networked television, or "smart glasses".

An effective acclimatization therapy might also be useful as a regular daytime "calming" therapy for an awake patient, simultaneously conditioning the patient and delivering calming benefits in itself. An effective acclimatization therapy might also be useful for SDB-comorbid insomniacs as a relaxing prelude to pressure support ventilation therapy, and/or as a sedative measure if arousal occurs during pressure support ventilation therapy. In such implementations, the acclimatization therapy may be invoked for a predetermined duration that is long enough for the patient to go to or return to sleep, such as thirty minutes. Alternatively, the acclimatization therapy may be terminated and pressure support ventilation therapy commenced once the sleep state algorithm 4328 determines that the patient has fallen asleep. The pressure support ventilation therapy may be terminated and acclimatization therapy re-commenced once the sleep state algorithm 4328 determines that the patient has awakened.

A yet further alternative is for the RPT device 4000 to terminate the acclimatization therapy and commence the pressure support ventilation therapy on receiving a command from the patient 1000. In one implementation of this alternative, the command is issued by actuating a manual control forming part of the user input devices 4220 of the RPT device 4000. In other implementations of this alternative, the command may be a sound emitted by the patient such as a vocal sound (e.g. a word or a hum), clap, or click. An audio sensor for receiving such a command may form part of the transducers 4270 of the RPT device 4000. Alternatively, the audio sensor may be located on a local external device 4288 that is in communication with the RPT device 4000 via the local network 4284. In a further implementation less disruptive to the relaxation of the patient, the command may be a voluntary respiratory manoeuvre or breathing pattern by the patient that is sensed via a transducer 4270. Such a respiratory manoeuvre may be, for example, a big sigh, a brief apnea/hypopnea, a succession of brief apneas/hypopneas, or repeated rapid cyclical bursts of inhalation/exhalation in a staccato fashion, etc.

8.8 Glossary

For the purposes of the present technology disclosure, in certain forms of the present technology, one or more of the following definitions may apply. In other forms of the present technology, alternative definitions may apply.

8.8.1 General

Air: In certain forms of the present technology, air may be taken to mean atmospheric air, and in other forms of the present technology air may be taken to mean some other combination of breathable gases, e.g. atmospheric air enriched with oxygen.

Respiratory Pressure Therapy (RPT): The application of a supply of air to an entrance to the airways at a treatment pressure that is typically positive with respect to atmosphere.

Continuous Positive Airway Pressure (CPAP) therapy: Respiratory pressure therapy in which the treatment pressure is approximately constant through a respiratory cycle of a patient. In some forms of CPAP therapy, the pressure at the entrance to the airways will be slightly higher during exhalation, and slightly lower during inhalation. In some forms, the pressure will vary between respiratory cycles of the patient, for example being increased in response to detection of indications of partial upper airway obstruction, and decreased in the absence of indications of partial upper airway obstruction.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Insomnia: Problems falling and staying asleep, or non-restorative sleep that persist(s) longer than one month and result in functional impairment. Two kinds of insomnia are observed:

(i) sleep onset insomnia: difficulty falling asleep;
(ii) sleep maintenance insomnia: frequent awakenings during the night or early morning awakenings.

Hyperarousal: A state of increased psychological and physiological tension marked by such effects as reduced pain tolerance, anxiety, exaggeration of startle responses, insomnia, fatigue and accentuation of personality traits.

Post-Traumatic Stress Disorder (PTSD): The development of characteristic symptoms following exposure to an extreme traumatic stressor event. The characteristic symptoms include persistent re-experiencing of the traumatic event (flashbacks), persistent avoidance of stimuli associated with the trauma, and persistent symptoms of increased arousal. All symptoms must persist for more than one month and cause clinically significant distress or impaired function. Post-traumatic stress disorder is common, frequently does not remit without intervention, and results in high levels of functional impairment and health care costs. Violent crimes, including rape and physical assaults, combat exposure, and natural disasters constitute examples of traumatic events that can involve threat to integrity of the self or others and can be accompanied by intense fear, helplessness, or horror. Community prevalence estimates of PTSD range from 1% to 10%, with higher estimates reported in victims of interpersonal violence (20% to 30%) and combat veterans (15%-30%).

Adherent: Continuing with treatment.

Compliant: Continuing with treatment for an extended duration.

8.8.2 Respiratory Cycle

Apnea: According to some definitions, an apnea is said to have occurred when flow falls below a predetermined threshold for a duration, e.g. 10 seconds. An obstructive apnea is said to have occurred when, despite patient effort, some obstruction of the airway does not allow air to flow. A central apnea is said to have occurred when an apnea is detected that is due to a reduction in breathing effort, or the absence of breathing effort, despite the airway being patent. A mixed apnea is said to have occurred when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: The state of affairs in a patient's respiration where an increase in effort by the patient does not give rise to a corresponding increase in flow rate. Where flow limitation occurs during an inspiratory portion of a breathing cycle it may be described as inspiratory flow limitation. Where flow limitation occurs during an expiratory portion of a breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is said to be a reduction in flow, but not a cessation of flow. In one form, a hypopnea may be said to have occurred when there is a reduction in flow below a threshold for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow during the inspiratory portion of the respiratory flow waveform.

Respiratory disturbance index (RDI): Apnea-Hypopnea Index plus RERA index.

Respiratory Event Related Arousal (RERA): A sequence of breaths lasting at least 10 seconds characterized by increasing respiratory effort or by flattening of the inspiratory portion of the flow rate waveform leading to arousal from sleep, when the sequence of breaths does not meet criteria for an apnea or hypopnea.

Respiratory flow rate, patient airflow rate, respiratory airflow rate (Qr): These synonymous terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

Inspiratory (inhalation) Time (Ti): The duration of the inspiratory portion of the respiratory flow rate waveform.

Expiratory (exhalation) Time (Te): The duration of the expiratory portion of the respiratory flow rate waveform.

Respiratory (total) Time (Ttot): The total duration between the start of one inspiratory portion of a respiratory flow rate waveform and the start of the following inspiratory portion of the respiratory flow rate waveform.

Typical recent ventilation: The value around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Upper-Airway Resistance Syndrome (UARS): A straightforward case of UARS includes all three of the following criteria: (1) increased esophageal pressure (respiratory effort) deflections; (2) associated with EEG arousals; and (3) having an objective criteria of excessive sleepiness. UARS is not universally accepted as a distinct syndrome, and instead may be incorporated under the title of Respiratory-Effort Related Arousal (RERA).

Ventilation (Vent): A measure of the total amount of gas being exchanged by the patient's respiratory system. Measures of ventilation may include one or both inspiratory and expiratory flow, per unit time. When expressed as a volume per minute, this quantity is often referred to as "minute ventilation". Minute ventilation is sometimes given simply as a volume, understood to be the volume per minute.

8.8.3 RPT Device Parameters

Flow rate (or flow): The volume (or mass) of air delivered per unit time. Flow rate may refer to an instantaneous quantity. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Leak: An unintended flow of air. In one example, leak may occur as the result of an incomplete seal between a mask and a patient's face. In another example leak may occur in a swivel elbow to the ambient.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

8.8.4 Terms for Ventilators

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not otherwise triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End Expiratory Pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$ revolution, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster, that is, a measure of the central tendency of the measures of ventilation over recent history.

Ventilator: A mechanical device that provides pressure support to a patient to perform some or all of the work of breathing.

8.8.5 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

8.8.6 Mathematical Terms

Fuzzy logic is used in a number of places in the present technology. The following is used to indicate a fuzzy membership function, which outputs a "fuzzy truth value" in the range [0, 1], 0 representing fuzzy false and 1 representing fuzzy true:

FuzzyMember (ActualQuantity, ReferenceQuantity1, FuzzyTruthValueAtReferenceQuantity1, ReferenceQuantity2, FuzzyTruthValueAtReferenceQuantity2, . . . , ReferenceQuantityN, FuzzyTruthValueAtReferenceQuantityN)

A fuzzy membership function is defined as $$FuzzyMember(x, x_1, f_1, x_2, f_2, \ldots, x_N, f_N) = \begin{cases} f_1, & x < x_1 \\ f_N, & x \geq x_N \\ InterpOnInterval(x, x_k, f_k, x_{k+1}, f_{k+1}), & x_k \leq x < x_{k+1}, 1 \leq k \leq N \end{cases}$$

where $$InterpOnInterval(x, x_k, f_k, x_{k+1}, f_{k+1}) = \begin{cases} f_k + \frac{(f_{k+1} - f_k)(x - x_k)}{x_{k+1} - x_k}, & x_k \neq x_{k+1} \\ f_k & \text{otherwise} \end{cases}$$

The $f_j$ are fuzzy truth values, and x and the $x_j$ are real numbers.

The function "Interp" is defined to be the same as "FuzzyMember", except that the values $f_k$ are interpreted as real numbers rather than fuzzy truth values.

The fuzzy "Or" of fuzzy truth values is the maximum of those values; the fuzzy "And" of fuzzy truth values is the minimum of these values. These will be indicated by the functions FuzzyOr and FuzzyAnd of two or more fuzzy truth values. It is to be understood that other typical definitions of these fuzzy operations would work similarly in the present technology.

"Exponential decay towards zero" with a time constant r means that during any period of decay starting at time t=T, the value of the decaying quantity V is given by $$V(t) = V(T) * \exp\left(-\frac{t - T}{\tau}\right)$$

8.9 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

| 8.10 REFERENCE SIGNS LIST | |
|---|---|
| patient | 1000 |
| patient interface | 3000 |
| seal-forming structure | 3100 |
| plenum chamber | 3200 |
| structure | 3300 |
| vent | 3400 |
| connection port | 3600 |
| forehead support | 3700 |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |
| pneumatic components | 4100 |
| air filters | 4110 |
| inlet air filter | 4112 |
| outlet air filter | 4114 |
| mufflers | 4120 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| supplemental oxygen | 4180 |
| electrical components | 4200 |
| PCBA | 4202 |
| power supply | 4210 |
| input devices | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local network | 4284 |
| remote external device | 4286 |
| local external device | 4288 |
| output device | 4290 |
| display driver | 4292 |
| display | 4294 |
| algorithms | 4300 |
| pre-processing module | 4310 |
| pressure compensation algorithm | 4312 |
| vent flow rate estimation algorithm | 4314 |
| leak flow rate estimation algorithm | 4316 |
| respiratory flow rate estimation algorithm | 4318 |
| jamming detection algorithm | 4319 |
| therapy engine module | 4320 |
| phase determination algorithm | 4321 |
| waveform determination | 4322 |
| ventilation determination algorithm | 4323 |
| inspiratory flow limitation determination algorithm | 4324 |
| apnea/hypopnea determination algorithm | 4325 |
| snore determination algorithms | 4326 |

-continued

| 8.10 REFERENCE SIGNS LIST | |
|---|---|
| target ventilation determination algorithm | 4327 |
| sleep state determination algorithm | 4328 |
| therapy parameter determination algorithm | 4329 |
| therapy control algorithm | 4330 |
| humidifier | 5000 |
| method | 7000 |
| steps | 7010 |
| step | 7020 |
| step | 7030 |
| step | 7040 |
| step | 7050 |
| process | 7059 |
| step | 7060 |
| step | 7070 |
| example histogram | 9000 |
| process | 10000 |
| step | 10010 |
| step | 10020 |
| step | 10030 |
| process | 11000 |
| step | 11010 |
| step | 11020 |

CITED REFERENCES

Krakow B, Ulibarri V A, Romero E A. *Patients With Treatment-Resistant Insomnia Taking Nightly Prescription Medications for Sleep: A Retrospective Assessment of Diagnostic and Treatment Variables*. Prim. Care Companion J Clin Psychiatry, 2010: 12(4).

The invention claimed is:

1. A method of control of a respiratory pressure therapy device to treat sleep disordered breathing (SDB)-comorbid hyperarousal disorders in a patient, the method comprising:
    controlling application of pressure support ventilation therapy to an airway of the patient by a respiratory pressure therapy device;
    controlling the respiratory pressure therapy device to auto-titrate an expiratory positive airway pressure (EPAP) of the pressure support ventilation therapy so as to maintain airway patency of the patient, such that the EPAP is bounded below by a floor pressure limit; and
    controlling, in the respiratory pressure therapy device, a determination of repeated adjustments to the floor pressure limit depending on events of interest during the auto-titration of the EPAP, wherein an adjustment to the floor pressure limit is dependent on a number of events of interest that occur in a predetermined interval during the auto-titration of the EPAP.

2. The method according to claim 1, wherein the adjustment to the floor pressure limit is dependent on a current value of the EPAP.

3. The method according to claim 1, wherein the adjustment to the floor pressure limit comprises incrementing the floor pressure limit if a predetermined number of events of interest occur within the predetermined interval.

4. The method according to claim 3, wherein incrementing the floor pressure limit comprises increasing the floor pressure to a current value of the EPAP.

5. The method according to claim 1, wherein the events of interest are SDB events.

6. The method according to claim 1, wherein the events of interest are increments to the EPAP as a result of the auto-titration of the EPAP.

7. The method according to claim 1, further comprising determining, in the respiratory pressure therapy device, a sleep state of the patient.

8. The method according to claim 7, wherein the auto-titrating the EPAP comprises not decreasing the EPAP while the patient is determined to be in an asleep state.

9. The method according to claim 7, wherein the pressure support ventilation therapy is applied dependent on the sleep state of the patient.

10. The method according to claim 9, wherein the respiratory pressure therapy device applies pressure support ventilation therapy when the patient is determined to be in an asleep state, and the respiratory pressure therapy device applies an acclimatisation therapy when the patient is determined to be in an awake state.

11. The method according to claim 10, wherein the acclimatisation therapy is paced breathing.

12. The method according to claim 11, wherein the paced breathing is combined with biofeedback matched to an interim breathing rate target of the paced breathing.

13. The method according to claim 12, where the biofeedback is in one or more of acoustic and visual form.

14. The method according to claim 1, further comprising applying the pressure support ventilation therapy on receiving, by the respiratory pressure therapy device, a command from the patient.

15. The method according to claim 14, wherein the command is activation of a manual control.

16. The method according to claim 14, wherein the command is a sound emitted by the patient.

17. The method according to claim 14, wherein the command is a voluntary respiratory manoeuvre by the patient.

18. A method of control of a respiratory pressure therapy device to treat sleep disordered breathing (SDB)-comorbid hyperarousal disorders in a patient, the method comprising:
    controlling application of pressure support ventilation therapy to an airway of the patient by a respiratory pressure therapy device;
    controlling the respiratory pressure therapy device to auto-titrate an expiratory positive airway pressure (EPAP) of the pressure support ventilation therapy so as to maintain airway patency of the patient, such that the EPAP is bounded below by a floor pressure limit; and
    controlling, in the respiratory pressure therapy device, a determination of repeated adjustments to the floor pressure limit depending on events of interest during the auto-titration of the EPAP, wherein the events of interest are increments to the EPAP, and the repeated adjustment of the floor pressure limit comprises repeatedly:
        forming a distribution of EPAP values at which increments to the EPAP occurred over an analysis interval, and
        adjusting the floor pressure limit based on statistical analysis of the distribution.

19. The method according to claim 18, wherein the adjustment of the floor pressure limit is based on a mode of the distribution.

20. The method according to claim 18, wherein the analysis interval is a night of pressure-support ventilation therapy with auto-titrating EPAP.

21. A sleep disordered breathing (SDB)-comorbid hyperarousal treatment apparatus comprising:
    a pressure generator configured to deliver a flow of air at a controllable treatment pressure above atmospheric to an airway of a patient via a patient interface over an air circuit; and
    a controller configured to:
        control the treatment pressure of the flow of air so as to apply pressure support ventilation therapy to the airway of the patient;
        auto-titrate an expiratory positive airway pressure (EPAP) of the pressure support ventilation therapy so as to maintain airway patency of the patient, such that the EPAP is bounded below by a floor pressure limit; and
        determine repeated adjustments to the floor pressure limit depending on events of interest during the auto-titration of the EPAP, wherein an adjustment to the floor pressure limit is dependent on a number of events of interest that occur in a predetermined interval during the auto-titration of the EPAP.

22. The SDB-comorbid hyperarousal treatment apparatus according to claim 21, further comprising a sensor configured to generate a signal representative of a physiological characteristic of the patient, wherein the controller is further configured to determine a sleep state of the patient from the signal.

23. The SDB-comorbid hyperarousal treatment apparatus according to claim 21, further comprising a user input device comprising a manual control.

24. The SDB-comorbid hyperarousal treatment apparatus according to claim 21, further comprising an audio sensor.

25. The SDB-comorbid hyperarousal treatment apparatus according to claim 21, further comprising a data communication interface through which the controller is configured to communicate with a local external device.

26. The SDB-comorbid hyperarousal treatment apparatus according to claim 25, wherein the controller is configured to control the local external device to provide biofeedback to the patient.

27. The SDB-comorbid hyperarousal treatment apparatus according to claim 25, wherein the controller is configured to receive an audio signal from the local external device.

28. The SDB-comorbid hyperarousal treatment apparatus according to claim 25, wherein the controller is configured to receive a signal representative of a physiological characteristic of the patient from the local external device, wherein the controller is further configured to determine a sleep state of the patient from the signal.

29. A sleep disordered breathing (SDB)-comorbid hyperarousal treatment apparatus comprising:
    a pressure generator configured to deliver a flow of air at a controllable treatment pressure above atmospheric to an airway of a patient via a patient interface over an air circuit; and
    a controller configured to:
        control the treatment pressure of the flow of air so as to apply pressure support ventilation therapy to the airway of the patient;
        auto-titrate an expiratory positive airway pressure (EPAP) of the pressure support ventilation therapy so as to maintain airway patency of the patient, such that the EPAP is bounded below by a floor pressure limit; and
        determine repeated adjustments to the floor pressure limit depending on events of interest during the auto-titration of the EPAP, wherein the events of interest are increments to the EPAP, and the repeated adjustment of the floor pressure limit comprises repeated:
   formation of a distribution of EPAP values at which increments to the EPAP occurred over an analysis interval, and
   adjustment of the floor pressure limit based on statistical analysis of the distribution.

\* \* \* \* \*